(12) United States Patent
Verner

(10) Patent No.: US 6,545,014 B2
(45) Date of Patent: *Apr. 8, 2003

(54) METHOD OF TREATING GLAUCOMA

(75) Inventor: Erik Joel Verner, Foster City, CA (US)

(73) Assignee: Texas Biotechnology Corporation, Houston, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 09/881,869

(22) Filed: Jun. 15, 2001

(65) Prior Publication Data

US 2002/0028829 A1 Mar. 7, 2002

Related U.S. Application Data

(62) Division of application No. 09/441,643, filed on Nov. 17, 1991, now Pat. No. 6,329,387, which is a continuation of application No. 09/148,643, filed on Sep. 4, 1998, now Pat. No. 6,013,655, which is a continuation of application No. 08/632,586, filed on Apr. 15, 1996, now Pat. No. 5,804,585.

(51) Int. Cl.$^7$ ............................................. A61K 31/435
(52) U.S. Cl. ...................... 514/301; 514/300; 514/302; 514/380
(58) Field of Search .................... 514/301, 302, 514/380

(56) References Cited

U.S. PATENT DOCUMENTS

| | | | |
|---|---|---|---|
| 2,888,455 A | 5/1959 | Kano et al. ............... 260/239.9 |
| 3,300,488 A | 1/1967 | Onoue et al. ............. 260/239.9 |
| 3,660,383 A | 5/1972 | Sumimoto et al. ........ 260/239.9 |
| 3,821,087 A | 6/1974 | Knazek et al. ............... 195/127 |
| 3,883,393 A | 5/1975 | Knazek et al. ............... 195/1.8 |
| 4,044,126 A | 8/1977 | Cook et al. .................. 424/243 |
| 4,161,599 A | 7/1979 | Maffrand .................... 546/114 |
| 4,191,554 A | 3/1980 | Gregory ........................ 71/95 |
| 4,311,845 A | 1/1982 | Braye et al. ................. 546/114 |
| 4,364,923 A | 12/1982 | Cook et al. ................... 424/46 |
| 4,375,544 A | 3/1983 | Meth-Cohn et al. ........ 546/114 |
| 4,406,898 A | 9/1983 | Lunn et al. .................. 424/246 |
| 4,414,209 A | 11/1983 | Cook et al. .................. 424/243 |
| 4,485,108 A | 11/1984 | Jozic .......................... 424/267 |
| 4,522,811 A | 6/1985 | Eppstein et al. ............... 514/2 |
| 4,577,014 A | 3/1986 | Lunn et al. .................... 544/22 |
| 4,585,773 A | 4/1986 | Dolak .......................... 514/253 |
| 4,659,369 A | 4/1987 | Levitt ............................ 71/92 |
| 4,752,613 A | 6/1988 | Floyd et al. ................. 514/438 |
| 4,753,672 A | 6/1988 | Levitt ............................ 71/92 |
| 4,769,371 A | 9/1988 | Atwal ......................... 514/275 |
| 4,861,366 A | 8/1989 | Levitt ............................ 71/90 |
| 4,997,836 A | 3/1991 | Sugihara et al. ............ 514/253 |
| 5,026,700 A | 6/1991 | Harrison et al. ............ 514/233 |
| 5,082,838 A | 1/1992 | Naka et al. .................. 514/211 |
| 5,114,918 A | 5/1992 | Ishikawa et al. .............. 514/11 |
| 5,187,195 A | 2/1993 | Oohata ........................ 514/610 |
| 5,198,548 A | 3/1993 | Beylin et al. ................ 546/136 |
| 5,208,243 A | 5/1993 | Peglion et al. .............. 514/309 |
| 5,230,999 A | 7/1993 | Suzuki et al. ................. 435/71 |
| 5,231,166 A | 7/1993 | Masaki et al. ............... 530/324 |
| 5,240,910 A | 8/1993 | Lam et al. ..................... 514/11 |

(List continued on next page.)

FOREIGN PATENT DOCUMENTS

| | | |
|---|---|---|
| AU | 5461286 | 3/1985 |
| AU | 8654612 | 10/1986 |
| CA | 2067288 | 10/1992 |

(List continued on next page.)

OTHER PUBLICATIONS

Allen et al., "The Cambridge crystallographic data centre: Computer–based search, retrieval, analysis and display of Information," *Acta Crystallogr.*, B35:2331–2339 (1979).

(List continued on next page.)

*Primary Examiner*—Bernard Dentz
(74) *Attorney, Agent, or Firm*—Stephanie L. Seidman; Dale L. Rieger; Heller Ehrman White & McAuliffe, LLP

(57) ABSTRACT

Methods, compositions, and compounds for modulating the activity of an endothelin peptide are provided. The methods use compositions that contain compounds that include those of the formula:

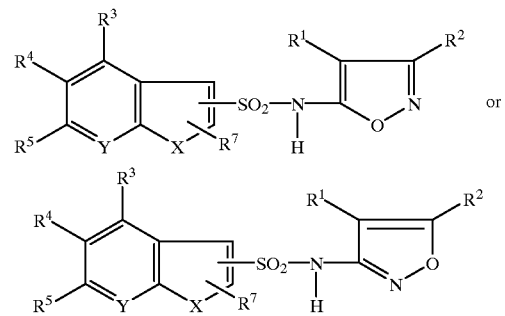

where X is selected from groups that include O, S, and NH; Y is selected from $O^+$ and N, and $R^1$ and $R^2$ are each selected independently from among alkyl, lower alkenyl, lower alkynyl, lower haloalkyl, halide, pseudohalide or H, except that $R^2$ is not halide. $R^3$, $R^4$ and $R^5$ are selected from among groups that include hydrogen, halide, alkoxy, alkyl, haloalkyl; and $R^7$ is selected from groups that include $(CH_2)_r R^{18}$, in which r is 0 to 6 and $R^{18}$ is selected from groups that include aryl, particularly pyrmidinyl and phenyl. The methods are effected by contacting endothelin receptors with one or more of the compounds or with compositions containing one or more of the compounds prior to, simultaneously with, or subsequent to contacting the receptors with an endothelin peptide.

3 Claims, No Drawings

U.S. PATENT DOCUMENTS

| | | | |
|---|---|---|---|
| 5,246,931 A | 9/1993 | Norbeck et al. | 514/242 |
| 5,248,807 A | 9/1993 | Fujimoto et al. | 560/75 |
| 5,260,276 A | 11/1993 | Cody et al. | 514/14 |
| 5,270,313 A | 12/1993 | Burri et al. | 514/252 |
| 5,292,740 A | 3/1994 | Burri et al. | 514/256 |
| 5,324,839 A | 6/1994 | Clemence et al. | 546/174 |
| 5,334,598 A | 8/1994 | Bagley et al. | 514/303 |
| 5,338,726 A | 8/1994 | Shiosaki et al. | 514/17 |
| 5,352,659 A | 10/1994 | Wakimasu et al. | 514/9 |
| 5,352,800 A | 10/1994 | Bills et al. | 548/539 |
| 5,378,715 A | 1/1995 | Stein et al. | 514/329 |
| 5,382,569 A | 1/1995 | Cody et al. | 514/17 |
| 5,389,620 A | 2/1995 | Ishikawa et al. | 514/80 |
| 5,389,633 A | 2/1995 | Miyake et al. | 514/233.2 |
| 5,407,941 A | 4/1995 | Carceller et al. | 514/290 |
| 5,420,123 A | 5/1995 | Murugesan | 514/220 |
| 5,420,129 A | 5/1995 | Breu et al. | 514/252 |
| 5,420,131 A | 5/1995 | Carceller et al. | 514/253 |
| 5,420,133 A | 5/1995 | Dhanoa et al. | 514/256 |
| 5,420,138 A | 5/1995 | Corbier et al. | 514/300 |
| 5,420,275 A | 5/1995 | Masuya et al. | 544/236 |
| 5,430,022 A | 7/1995 | Hemmi et al. | 514/18 |
| 5,439,887 A | 8/1995 | Hamon et al. | 514/13 |
| 5,444,152 A | 8/1995 | Ishikawa et al. | 530/331 |
| 5,464,853 A | 11/1995 | Chan et al. | 514/378 |
| 5,470,833 A | 11/1995 | Ishikawa et al. | 514/18 |
| 5,492,892 A | 2/1996 | Anderson et al. | 514/13 |
| 5,514,691 A | 5/1996 | Chan et al. | 514/312 |
| 5,514,696 A | 5/1996 | Murugesan et al. | 514/380 |
| 5,543,521 A | 8/1996 | Chan et al. | 544/349 |
| 5,565,485 A | 10/1996 | Bagley et al. | 514/452 |
| 5,571,821 A | 11/1996 | Chan et al. | 514/312 |
| 5,585,397 A | 12/1996 | Tung et al. | 514/473 |
| 5,589,478 A | 12/1996 | Yamada et al. | 514/269 |
| 5,591,728 A | 1/1997 | de Nanteuil et al. | 514/80 |
| 5,591,761 A | 1/1997 | Chan et al. | 514/380 |
| 5,594,021 A | 1/1997 | Chan | 514/378 |
| 5,599,811 A | 2/1997 | Berryman et al. | 514/226.5 |
| 5,612,359 A | 3/1997 | Murugesan | 514/365 |
| 5,641,793 A | 6/1997 | Bradbury | 514/352 |
| 5,668,137 A | 9/1997 | Phillips et al. | 514/255 |
| 5,668,176 A | 9/1997 | Bagley et al. | 514/569 |
| 5,726,194 A | 3/1998 | Osswald et al. | 514/362 |
| 5,783,705 A | 7/1998 | Blok et al. | 548/247 |
| 5,804,585 A | 9/1998 | Verner | 514/301 |
| 5,827,869 A | 10/1998 | Murugesan | 514/374 |
| 5,958,905 A | 9/1999 | Chan et al. | 514/92 |
| 5,962,490 A | 10/1999 | Chan et al. | 514/380 |
| 5,977,117 A | 11/1999 | Chan et al. | 514/256 |
| 6,013,655 A | 1/2000 | Verner | 514/301 |
| 6,017,916 A | 1/2000 | Berryman et al. | 514/233.8 |
| 6,017,951 A | 1/2000 | Patt et al. | 514/464 |
| 6,030,991 A | 2/2000 | Chan et al. | 514/380 |
| 6,043,241 A | 3/2000 | Cheng et al. | 514/233.8 |
| 6,043,265 A | 3/2000 | Murugesan et al. | 514/374 |
| 6,060,475 A | 5/2000 | Bradbury et al. | 514/255 |
| 6,063,911 A | 5/2000 | Vournakis et al. | 536/20 |
| 6,080,774 A | 6/2000 | Murugesan et al. | 514/380 |
| 6,083,951 A | 7/2000 | Bradbury | 514/256 |
| 6,083,955 A | 7/2000 | Harada et al. | 514/269 |
| 6,107,320 A | 8/2000 | Murugesan et al. | 514/379 |
| 6,133,263 A | 10/2000 | Cheng et al. | 514/233.8 |
| 6,133,442 A | 10/2000 | Breu et al. | 544/123 |
| 6,248,767 B1 | 7/2001 | Blok et al. | 514/380 |
| 6,265,428 B1 | 7/2001 | Chan et al. | 514/396 |
| 6,329,387 B2 | 12/2001 | Verner | 514/301 |

FOREIGN PATENT DOCUMENTS

| | | |
|---|---|---|
| CA | 2071193 | 12/1992 |
| EP | 0177163 | 8/1985 |
| EP | 0248399 | 12/1987 |
| EP | 0404525 | 12/1990 |
| EP | 0405421 | 1/1991 |
| EP | 0411150 | 2/1991 |
| EP | 0436189 | 7/1991 |
| EP | 0457195 | 11/1991 |
| EP | 0460679 | 12/1991 |
| EP | 0496452 | 7/1992 |
| EP | 0558258 | 9/1993 |
| EP | 0569193 | 11/1993 |
| EP | 0626174 | 11/1994 |
| EP | 0640596 | 3/1995 |
| EP | 0682016 A1 | 11/1995 |
| EP | 0702012 A1 | 3/1996 |
| EP | 0725067 A1 | 8/1996 |
| EP | 0768305 A1 | 4/1997 |
| GB | 0804036 | 11/1958 |
| GB | 1473433 | 5/1977 |
| GB | 2259450 | 3/1993 |
| JP | 60188084 | 9/1985 |
| JP | 60188088 | 9/1985 |
| JP | 63238006 | 4/1990 |
| JP | 4134084 | 5/1992 |
| WO | 9115479 | 10/1991 |
| WO | 9308799 | 5/1993 |
| WO | 9403483 | 2/1994 |
| WO | 9427979 | 12/1994 |
| WO | 9503044 | 2/1995 |
| WO | 9503295 | 2/1995 |
| WO | 9513262 | 5/1995 |
| WO | 9524385 | 9/1995 |
| WO | 9604759 | 4/1996 |
| WO | 9631492 | 10/1996 |
| WO | 9725321 | 7/1997 |
| WO | 9735864 | 10/1997 |
| WO | 9739000 | 10/1997 |
| WO | 9813366 | 4/1998 |
| WO | 9849162 | 11/1998 |
| WO | 0149289 | 7/2001 |
| WO | 0149685 | 7/2001 |

OTHER PUBLICATIONS

Anagnostou et al., "Erythropoietin has mitogenic and positive chemotactic effects on endothelial cells," *P.N.A.S.*, 87:5978–5982 (1990).

Arai et al., "Cloning and expression of a cDNA encoding an endothelin receptor," *Nature*, 348:730–732 (1990).

Aumelas et al., "Determination of the structure of [Nle$^7$]–endothelin by $^1$H NMR," *Int. J. Peptide Protein Res.*, 37:315–324 (1991).

Balasubramanian, R., "New type of representation for mapping chain folding in protein molecules," *Nature*, 266:856–857 (1977).

Benigni et al., "A specific endothelin subtype A receptor antagonist protects against injury in renal disease progression," *Kidney International* 44:440–444 (1993).

Bolger et al., "Characterization of binding of the Ca$^{++}$ channel antagonist [$^3$H] nitrendipine, to guinea–pig ileal smooth muscle," *J. of Pharmacology and Experimental Therapeutics*, 225:291–309 (1983).

Bolger et al., "Vascular reactivity, tissue levels, and binding sites for endothelin: A comparison in the spontaneoulsy hypertensive and Wistar–Kyoto rats," *Can. J. Physiol. Pharm.*, 69:406–413 (1990).

Borges et al., "Tissue selectivity of endothelin," *Eur. J. of Pharmacology*, 165:223–230 (1989).

Brint et al., "Upperbound procedures for the identification of similar three-dimensional chemical stuctures," *J. Comput.–Aided Mol. Design*, 2:311–310 (1988).

Brooks et al., "Effect of nifedipine on cyclosporine A–induced nephrotoxicity, urinary endothelin excretion and renal endothelin receptor number," *Eur. J. of Pharmacology*, 194:115–117 (1991).

Buemi et al., "Influence of recombinant erythropoietin on the production of endothelin–1 from human umbilical artery," *Nephron*, 64(1):165–166 (1993).

CA: 107(13)108750m, 1987.
CA: 74(17)86290g, 1970.
CA: 68(21)94582v, 1967.
CA: 67(5)21903v, 1966.
CA: 109(18)162247g, 1988.
CA: 72(19)100676e, 1970.
CA: 70(15)68350q, 1968.
CA: 108(11)94444w, 1987.
CA: 107(9)74639q, 1987.
CA: 117(25)245036d, 1992.
CA: 120(9)94890m, 1991.
CA: 66(15)65458n, 1967.
CA: 119(25)262066x, 1993.
CA: 107(9)74639q, 1987.
CA: 109(3)16570r, 1988.
CA: 105(13)107865z, 1986.
CA: 114(3)17049t, 1990.
CA: 107(23)215074r, 1987.
CA: 119(7)65021c, 1993.
CA: 114(11)95016u, 1990.
CA: 67(7)32627j, 1966.
CA: 108(23)197876t, 1988.
CA: 110(14)121203s, 1988.
CA: 114(7)55340p, 1990.
CA: 68(9)39615h, 1967.
CA: 78(1)77r, 1972.
CA: 75(1)5884z, 1970.
CA: 116(21)213114r, 1992.
CA: 76(13)68021g, 1971.
CA: 107(13)108750m, 1987.
CA: 117(3)19848p, 1992.
CA: 76(15)85737n, 1971.
CA: 108(9)68228j, 1987.
CA: 67(3)11468t, 1966.
CA: 116(5)40956m, 1991.
CA: 116(23)235529g, 1991.
CA: 110(15)135176x, 1987.
CA: 70(13)57821t, 1968.
CA: 117(13)124085k, 1992.
CA: 114(17)156647z, 1991.
CA: 107(13)108750m, 1987.
CA: 93(19)179284r, 1980.
CA: 104(25)218557z, 1986.
CA: 80(25)146111k, 1974.
CA: 107(23)215074r, 1987.
CA: 107(13)108750m, 1987.
CA: 106(1)110t, 1985.
CA: 114(17)156648a, 1991.
CA: 115(23)247397e, 1991.
CA: 111(9)74672c, 1989.
CA: 110(21)185301e, 1989.
CA: 108(7)54535v, 1988.
CA: 107(23)215074r, 1987.
CA: 71(26)128748h, 1967.
CA: 73(23)120511w, 1970.
CA: 70(9)37686z, 1968.
CA: 120(13)158152g, 1993.
CA: 120(12)144337j, 1993.
CA: 66(1)1504s, 1966.
CA: 69(2)5219n, 1968.
CA: 72(19)100676e, 1970.
CA: 66(15)65458n, 1967.
CA: 69(9)36111a, 1967.
CA: 110(21)185301e, 1989.
CA: 120(12)144339m, 1993.
CA: 120(9)105206w, 1993.
CA: 102(21)182241j, 1985.
CA: 102(17)147630p, 1985.
CA: 103(19)153413g, 1985.
CA: 82(17)110544f,1974.
CA: 96(6)40928x, 1981.
CA: 73(19)98851h, 1970.
CA: 80(2)6932d, 1973.
CA: 104(25)218557z, 1986.
CA: 106(7)43380y, 1986.
CA: 106(1)110t, 1985.
CA: 105(13)107865z, 1986.
CA: 70(19)87639g, 1968.
CA: 69(3)10427h, 1967.
CA: 98(25)215517h, 1982.
CA: 108(9)68229k, 1987.
CA: 74(17)87945m, 1970.
CA: 74(11)53764m, 1970.
CA: 73(23)117784g, 1969.
CA: 67(5)21903v, 1966.
CA: 107(9)74639q, 1987.
CA: 102(21)182241j, 1985.
CA: 74(23)125679n, 1970.
CA: 70(1)4102c, 1968.
CA: 101(16)137107p, 1984.
CA: 76(11)56259c, 1971.
CA: 87(1)631c, 1977.
CA: 73(23)120511w, 1967.
CA: 84(11)73173c, 1975.
CA: 80(17)95868c, 1974.
CA: 77(17)113370d, 1972.
CA: 94(23)192202c, 1980.
CA: 70(19)87635c, 1968.
CA: 83(23)191975t, 1975.
CA: 77(13)83384s, 1972.
CA: 111(7)57717d, 1988.
CA: 70(1)4103d, 1965.
CA: 80(25)146111k, 1974.
CA: 66(19)85762k, 1967.

Cardell et al., "Two functional endothelin receptors in guinea–pig pulmonary arteries," *Neurochem. Int.*, 18(4):571–574 (1991).

Carlini et al., "Intravenous erythropoietin (rHuEPO) administration increases plasma endothelin and blood pressure in hemodialysis patients," *Am. J. Hyper.*, 6:103–107 (1993).

Castiglione et al., "Alanine scan of endothelin," Peptides: Chemistry and Biology, Proc. Amer. Rept. Symp. (Twelfth), J.A. Smith and J.E. Rivier, Eds., ESCOM, Leiden, 1992, pp. 402–403.

Chemical abstract (CA): 112(19)178747t, 1987.

Chemical abstract (CA): 112(19)178747t.

Chemical Abstracts vol. 65, abstract No. 14649g, citing Uno et al., *Chem. Pharm. Bull.* 14:756–762 (1966).

Clarke et al., "Endothelin is a potent long–lasting vasoconstrictor in men," Am. J. Physiol., 257(6 pt 2):H2033–H2035 (1989).

Clozel et al., "Pathophysiological role of endothelin revealed by the first orally active endothelin receptor antagonist", Nature 365:759–761, (1993).

Cody et al., "The rational design of a highly potent combined $ET_A$ and $ET_B$ receptor antagonist (PD145065) and related analogues," Med. Chem. Res., 3:154–162 (1993).

Cooper et al., "A novel approach to molecular similarity," J. Comput.–Aided Mol. Design, 3:253–259 (1989).

Database Crossfire Beilstein Registry No. 1021364 and 1086426, citing Saito et al., Yakugaku Zasshi 88:1289, 1292 (1968).

De Castiglione et al., Alanine scan of endothelin, in Peptides: Chemistry and Biology, Proc. Amer. Rept. Symp. (Twelfth), (J.A. Smith and J.E. Rivier, Eds.) ESCOM, Leiden, 1992, pp. 402–403.

De Nucci et al., "Pressor effects of circulating endothelin are limited by its removal in the pulmonary circulation and by the release of prostacyclin and endothelium–derived relaxing factor," Proc. Natl. Acad. Sci., 85:9797 (1988).

Doherty, "Endothelin: A new challenge," J. Medicinal Chem., 35(9):1493–1508 (1992).

Endothelin, Receptor Antagonist (TBC 11251), Research and Development—Compounds Under Development, pp. 3–5 (available at http://www.tbc.com/resrch.htm on Sep. 3, 1997).

Eschbach et al., "Recombinant human erythropoietin in anemic patients with end stage renal disease; results of a phase III multicenter clinical trial," Ann. Intern. Med., 111:992–1000 (1989).

Filep et al., "Endothelin–1 induces prostacyclin release from bovine aortic endothelial cells," Biochem. and Biophys. Research Comm., 177(1):171–176 (1991).

Fujimoto and Sakai, "Synthesis and Structure of N1–Acylated Sulfiodizole and its homologues", Chem. Pharm. Bull. 14(3):280–284 (1966). Certified English translation provided.

Fujimoto et al., "A novel non–peptide endothelin antagonist isolated from bayberry," FEBS 305(1):41–44 (1992).

Fujimoto et al., "Isoxazole derivatives. II. Synthesis and structure of N–acylsufodiazoles and their homologs," Chemical Abstracts, vol. 65, No. 2, Jul. 18, 1966, Abstract No. 2241eq.

Furchgott and Zawadzki et al., "The obligatory role of endothelial cells in the relaxation of arterial smooth muscle by acetylcholine", Nature 288:373–376, (1980).

Galantino et al., "D–Amino acid scan of endothelin," Peptides: Chemistry & Biology, Proc. Amer. Report. Symp. (Twelfth), J.A. Smith and J.E. Rivier, Eds., ESCOM, Leiden, 1992, pp. 404–405.

Gu et al., "The inhibitory effect of [D–Arg$^1$, D–Phe, D–Try$^{7,9}$, Leu$^{11}$] substance P on endothelin–1 binding sites in rat cardiac membranes," Biochem. and Biophys. Research Commun., 179(1):130–133 (1991).

Heidenreich et al., "Erythropoietin induces contraction of isolated renal small resistance vessels," Nephrol. Dial. Transplant, 5:739–740 (1990).

Hiley et al., "Functional studies on endothelin catch up with molecular biology," Trends Pharmacol. Sci., 10:47–49 (1989).

Hirata et al., "Receptor binding activity and cytosolic free calcium response by synthetic endothelin analogs in culture rat vascular smooth muscle cells," Biochem. and Biophys. Research Commun., 160:228–234 (1989).

Hori et al., "Hemodynamics and volume changes by recombinant human erythropoietin (rHuEPO) in the treatment of anemic hemodialysis patients," Clin. Nephrol., 33:293–298 (1990).

Ihara et al., "An endothelin receptor ($ET_A$) antagonist isolated from Streptomyces misakiensis," Biochem. and Biophys. Research Commun., 178(1):132–137 (1991).

Ihara et al., "Biological profiles of highly potent novel endothelin antagonists selective for the $ET_A$ receptor," Life Sciences, 50:247–255 (1991).

Inoue et al., "The human endothelin family: Three structurally and pharmacologically distinct isopeptides predicted by three separate genes," Proc. Natl. Acad. Sci. USA, 86:2863–2867 (1989).

Ishikawa et al., "Cyclic pentapeptide endothelin antagonists with high $ET_A$ selectivity. Potency– and solubility–enhancing modifications," J. Med. Chem., 35:2139–2142 (1992).

IUPAC–IUB Commission on Biochemical Nomenclature, Biochem. 11:942–944, (1972).

Kaltenbronn et al., "Renin inhibitors containing isosteric replacements of the amide bond connecting the $P_3$ and $P_2$ sites," J. Med. Chem., 33:838–845 (1990).

Kanno et al., "Endothelin–1 and Vasculitis", J. Amer. Med. Assoc. 264:2868, (1990).

Karplus, M., "Molecular Dynamics: Applications to Proteins," in Computer Simulation of Chemical and Biomolecular Systems, (Bevendge and Jorfensen, Eds.) Annals of the New York Acad. Science, 482:255–266 (1986).

Kashiwabara et al., "Putative precursors of endothelin have less vasoconstrictor activity in vitro but a potent pressor effect in vivo," FEBS Letters, 247(1):73–76 (1989).

Kemp, D.S., "Peptidomimetics and the template approach to nucleation of β–sheets and α–helices in peptides," Tibtech, 8:249–255 (1990).

Klemm et al., Chemistry of thienopyridines. III. Synthesis of thieno[2,3,–b]– and thieno[2,3–b]pyridine systems, J. Org. Chem., 34:347–354 (1969).

Kloog et al., "Similarities in mode and sites of action of sarafotoxins and endothelins," Trends Pharmacol. Sci., 10:212–214 (1989).

Koyama et al., "Plasma endothelin levels in patients with uremia," Lancet, 1(8645):991–992 (1989).

Kurihara et al., "The possible role of endothelin–1 in the pathogenesis of coronary vasospasm", J. Cardiovas. Pharmacol. 13:Suppl. 5, S132–S142, (1989).

Lerman et al., "Circulating and tissue endothelin immunoreactivity in advanced atherosclerosis", New Engl. J. Med. 325:997–1001, (1991).

LexPat Record of U.S. patent No. 5,464,853.

Lin et al., A cephalotaxine synthesis founded on a mechanistically interesting, quasi–biomimetic strategy, J. Am. Chem. Soc. 116:9791–9792 (1994).

Maggi et al., "Potent contractile effect of endothelin in isolated guinea–pig airways," Eur. J. Pharmacol., 160:179–182 (1989).

Martin et al., "Identification and characterization of endothelin binding sites in rat renal papillary and glomerular membranes," Biochem. Biophys. Res. Commun., 162:130–137 (1989).

McMahon et al., Effect of phosphoramidon (endothelin converting enzyme inhibitor) and BQ–123 (endothelin receptor subtype A antagonist) on blood pressure in hypertensive rats, *Am. J. Hypertension* 6(8):667–673 (1993).

Miyata et al., "WS–7338, new endothelin receptor antagonists isolated from Streptomyces sp. No. 7338," *J. Antibiotics*, 45(1):74–82 (1992).

Miyata et al., "WS009 A and B, new endothelin receptor antagonists isolated from Streptomyces sp. No. 89009," *J. Antibiotics*, 45(7):1029–1040 (1992).

Miyata et al., WS009 A and B, new endothelin receptor antagonists isolated from Streptomyces sp. No. 89009, *J. Antibiotics* 45(7):1041–1046 (1992).

Miyauchi et al., "Increase of the function of intra–cardiac autonomic nerves in isolated atria of swim–trained rats: study by the intra–cardiac nerve stimulation", *Jpn. J. Pharmacol.* 58:279, (1992).

Morel et al., "Increased plasma and pulmonary lymph levels of endothelin during endotoxin shock," *Eur. J. Pharm.*, 167:427–428 (1989).

Nakajima et al., "Endothelin–binding inhibitors, BE–18257A and BE–18257B II. Structure determination," *J. Antibiotics*, 44(12):1348–1356 (1991).

Nakajima et al., "Synthesis of endothelin–1 analogues, endothelin–3, and sarafotoxin S6b: Structure–activity relationships," *J. of Cardiovascular Pharm.*, 13(Suppl. 5):S8–S12 (1989).

Nelson et al., Chemical and biological factors influencing drug biotransformation, *Analyt. Biochem.*, selected pages (1987).

Nirei et al., "An endothelin $et_A$ receptor antagonist, FR139317, Amerliorates cerebral vasospasm in dogs", *Life Sci.* 52:1869–1874, (1993).

Nishikibe et al., "Antihypertensive effect of a newly synthesied endothelin antagonist, BQ–123, in a genetic hypertensive model," *Life Sci.* 52:717–724 (1993).

Nishikori et al., "Receptor binding affinity and biological activity of C–terminal elongated forms of endothelin–1," *Neurochem. Int.*, 18(4):535–539 (1991).

Nogrady et al., "4–pro–drugs and soft drugs", *Medicinal Chemistry A Biochemical Approach*:pp. 388–392, (1985).

Nonnast–Daniel et al., "Atrial natriuretic peptide and central hemodynamics during correction of renal anemia by recombinant human erythropoietin treatment in regular dialysis treatment patients," *Nephrol Dial Transplant*, 4:478 (1989).

Official Gazette Notice, Jul. 7, 1998, "Adverse Decisions in Interference", Interference No. 103,876.

Ogawa et al., "Molecular cloning of a non–isopeptide–selective human endothelin receptor," *Biochem. and Biophys. Research Comm.*, 178(1):248–255 (1991).

Ohashi et al., "Asterric acid, a new endothelin binding inhibitor," *J. Antibiotics*, 45(10):1684–1685 (1992).

Ormsbee et al., Production of hypertension with desoxycorticosterone acetate–impregnated silicone rubber implants, *J. Pharm. Sci.* 62(2):255–257 (1973).

Palmer et al., "Nitric oxide release accounts for the biological activity of endothelium–derived relaxing factor," *Nature*, 327:524–526 (1987).

Panek et al., "Endothelin and structurally related analogs distinguish between endothelin receptor subtypes," *Biochem. and Biophys. Research Commun.*, 183(2):566–571 (1992).

Perkins et al., Proposed solution structure of endothelin, *Int. J. Peptide Protein Res.*, 36:128–133 (1990).

Press Release, Texas Biotechnology Corporation, Evaluation of novel, highly selective Eta receptor antagonists in hypoxia–induced pulmonary hypertension, Oct. 14, 1999, located at http://www.tbc.com/.

Press Release, Texas Biotechnology Corporation, Endothelin antagonism inhibits pulmonary vascular remodeling in the hypoxic piglet, Oct. 14, 1999, located at http://www.tbc.com/.

Press Release, Texas Biotechnology Corporation, Discovery of potent, orally available, ETa selective endothelin antagonists: TBC3711, Oct. 14, 1999, located at http://www.tbc.com/.

Press Release, Texas Biotechnology Corporation, Antihypertensive effects of prolonged treatment with oral TBC11251NAa, a novel selective ETa endothelin receptor antagonist, in spontaneously hypertensive hamsters, Oct. 14, 1999, located at http://www.tbc.com/.

Raine et al., Effect of erythropoietin on blood pressure, *Am. J. Kid Dis.*, 18(suppl):76–82 (1991).

Raju et al., Thiophenesulfonamides as endothelin receptor antagonists, *Bioorganic Medicinal Chem. LETT.* 6(22):2651–2656 (1996).

Raju et al., Amide bond surrogates: a study in thiophenesulfonamide based endothelin receptor antagonists, *Bioorganic Medicinal Chem. LETT.* 7(7):939–944 (1997).

Raju et al., Search for surrogates: a study of endothelin receptor antagonist structure activity relationships, *Bioorganic Medicinal Chem. LETT.*7(7): 933–938 (1997).

Ramachandran et al., "Conformation of polypeptides and proteins," *Adv. Prot. Chem.*, 23:283–437 (1968).

Ray et al., "Circulating endothelin in acute ischaemic syndromes", *Br. J. Heart J.* 67:383–386, (1992).

Saeki et al., "[Ala$^{1,3,11,15}$] endothelin–1 analogs with $ET_B$ agonistic activity," *Biochem. and Biophys. Research Commun.*, 179(1):286–292 (1991).

Saida et al., "A novel peptide, vasoactive intestinal contractor, of a new (endothelin) peptide family," *J. Biol. Chem.*, 264(25):14613–14616 (1989).

Saito et al., "Application of monoclonal antibodies for endothelin to hypertensive research," *Hypertension*, 15:734–738 (1990).

Sakurai et al., "Cloning of a cDNA encoding a non–isopeptide–selective subtype of the endothelin receptor," *Nature*, 348:732–735 (1990).

Samtleben et al., "Blood pressure change during treatment with recombinant human erythropoietin," *Contrib. Nephrol.*, 66:114–122 (1988).

Sanjay et al., "Does PTCA increase circulating endothelin level in Man?", *Circulation* 84:(Suppl. 4):726, (1991).

Saudek et al., "Solution conformation of endothelin–1 by $^1$H NMR, CD, and molecular modeling," *Int. J. Peptide Protein Res.*, 37:174–179 (1991).

Saudek et al., "$^1$H–NMR study of endothelin, sequence–specific assingment of the spectrum and a solution structure," *FEBS Letters*, 257(1):145–148 (1989).

Schafer et al., "Treatment of renal anemia with recombinant human erythropoietin," *Am. J. Nephrol.*, 8:352–362 (1989).

Schvartz et al., "Bovine cerebellum endothelin receptor: Solubilization and identification," *Endocrinology*, 126(6):3218–3222 (1990).

Shimazaki et al., "Piperazine derivatives," *Chem. Abstracts*, 106:558 (abst. No. 33114a). (1987).

Simonson et al., "Endothelin–1 stimulates contraction of rat glomerular mesangial cells and potentiates β–Adrenergic–mediated cyclic adenosine monophosphate accumulation," *J. Clin. Invest.*, 85:790–797 (1990).

Spinella et al., "A proposed structural model of endothelin," *Peptide Research*, 2(4):286–291 (1989).

Spinella et al., "Design and synthesis of a specific endothelin 1 antagonist: Effects on pulmonary vasoconstriction," *Proc. Natl. Acad. Sci. USA*, 88p:7443–7446 (1991).

Spokes et al., "Studies with endothelin–3 and endothelin–1 on rat blood pressure and isolated tissues: Evidence for multiple endothelin receptor subtypes," *J. of Cardiovascular Pharmacology*, 13(Suppl. 5):S191–S192 (1989).

Stein et al., "The Discovery of Sulfonamide Endothelin Antagonists and the Development of the Orally Active $ET_A$–Antagonist 5–(Dimethylamino)–N–(3, 4–dimethyl–5–isoxazolyl)–1–naphthalenesulfonamide," *J. Med. Chem.*, 37(3):329–331 (1994).

Stein et al., The discovery . . . –1–naphthalenesulfonamide, pp. 21–22, CA 120:18233n.

Stewart et al., "Increased plasma endothelin–1 in pulmonary hypertension: marker or mediator of disease?" *Ann. Int. Med. 114*:464–469, (1991).

Sundal et al, "Correction of anemia of chronic renal failure with recombinant human erythropoietin:Safety and efficacy of one year's treatment in a European multicenter study of 150 hemodialysis–dependent patients," *Nephrol Dail Transplant*, 4:979–987 (1989).

Szelke et al, "Novel transition–state analogue inhibitors of renin," *In Peptides: Structure and Function, Proceedings of the Eighth American peptide symposium*, (Hruby and Rich, Eds.); pp. 579–582, Pierce Chemical Co., Rockford, Illinois (1983).

Tahara et al., "Circulating immunoreactive endothelin in patients undergoing percutaneous transluminal coronary angioplasty", *Metab. Clin. Exp. 40*:1235–1237, (1991).

Takayanagi et al., "Presence of non–selective type of endothelin receptor on vascular endothelium and its linkage to vasodilation," *FEBS Letters*, 282(1):103–106 (1991).

Takayanagi et al., "Multiple subtypes of endothelin receptors in porcine tissues: characterization by ligand binding, affinity labeling and regional distribution," *Reg. Pep.*, 32:23–37 (1991).

Texas Biotechnology Receives U.S. Patents For New Class of Cardiovascular Therapeutics, Endothelin A Receptor Antagonists, Houston, TX, Jan. 22, 1997, (available at http://www.tbc.com/press/pr012297.html on Jan. 13, 1999).

Texas Biotechnology Announces Initiation of Phase 1 Clinical Trial For TBC 1269 To Treat Asthma, Houston, TX, Jan. 21, 1997, For Immediate Release, (available at http://www.tbc.com/PR012197.HTM on Sep. 05, 1997).

Texas Biotechnology Receives First Patent Issued For New Class of Cardiovascular Drugs, Houston, TX, Dec. 6, 1995, For Immediate Release, (available at http://www.tbc.com/press/pr120695.html on Jan. 27, 1999).

Texas Biotechnology Announces Initiation of Phase 1 Clinical Trial For TBC 11251 To Treat Congestive Heart Failure, Houston, TX, Nov. 13, 1996, For Immediate Release, (available at http://www.tbc.com/PR111396.HTM on Sep. 05, 1997).

Texas Bioctechnology Announces Preliminary Phase II Results of Novastan In Acute Myocardial Infarction, Houston, TX, Oct. 21, 1996, For Immediate Release (available at http://www.tbc.com/press/pr102196.html on Jan. 28, 1999).

Texas Biotechnology Signs Additional Clinical Development Agreement With Synthelabo For Novastan®, Houston, TX, Jun. 25, 1996, For Immediate Release, (available at http://www.tbc.com/press/pr062596.html on Jan. 28, 1999).

Texas Biotechnology Resubmits Novastan® NDA, Houston, TX, Mar. 22, 1999, For Immediate Release (available at http://www.tbc.com/press/pr032299.html on May 27, 1999).

Texas Biotechnology Reports Additional Positive Phase IIA Trial Results In Congestive Heart Failure, Houston, TX, Jul. 21, 1998, For Immediate Release, (available at http:www.tbc.com/press/pr072298.html on Jan. 28, 1999).

Texas Biotechnology Initiates Phase III Trial For Novastan® in Coronary Interventional Procedures, Houston, TX, May 9, 1996, For Immediate Release, (available at http://www.tbc.com/presspr050996.html on Jan. 28, 1999).

Texas Biotechnology Presents Clinical Results on its Endothelin A Receptor Antagonist, TBC11251, at AHA Sessions, Houston, TX, Nov. 10, 1998, *For Immediate Release*, (available at http://www.tbc.com/press/pr111098.html on Jan. 13, 1999).

Texas Biotechnology Initiates Filing of New Drug Application For Novastan®, Houston, TX, Jul. 2, 1997, For Immediate Release (available at http://www.tbc.com/press/pr070297.html on Jan. 28, 1999).

Texas Biotechnology Presents Clinical Results on its Endothelin A Receptor Antagonist, TBC11251, at HA Sessions, Houston, TX, Nov. 10, 1998, For Immediate Release, (available at http://www.tbc.com/press/pr111098.html on Jan. 28, 1999).

Texas Biotechnology Reports Endothelin A Receptor Antagonist and VCAM/VLA–4 Inhibitor Patents, Houston, TX, May 16, 1996, For Immediate Release, (available at http://www.tbc.com/PR051696.HTM on Sep. 05, 1997).

Texas Biotechnology Completes Phase I Safety Trial For Oral Endothelin Antagonist, Houston, TX, Dec. 11, 1997, For Immediate Release (available at http://www.tbc.com/press/pr121197.html on Jan. 28, 1999).

Texas Biotechnology And Loyola University Medical Center Sponsor International Symposium On Heparin–Induced Thrombocytopenia And New Thrombin Inhibitors, Houston, TX, Dec. 6, 1996, For Immediate Release, (available at http://www.tbc.com/press/pr120696.html on Jan. 28, 1999).

Texas Biotechnology Reports Positive Phase IIA Trial Results of Endothelin Receptor Antagonist in CHF, Houston, TX, Feb. 11, 1998, *For Immediate Release*, (available at http://www.tbc.com/press/pr021198.html on Jan. 13, 1999).

Texas Biotechnology Reports Phase II Clinical Trial Results, Houston, TX, Feb. 21, 1996, For Immediate Release, (available at http://www.tbc.com/press/pr022196.html on Jan. 28, 1999).

Texas Biotechnology Announces Clinical Agreements With Synthelabo, Houston, TX, Jan. 22, 1996, For Immediate Release, (available at http://www.tbc.com/press/pr012296.html on Jan. 28, 1999).

Texas Biotechnology Announces Results of Phase III Novastan® Clinical Study In Patients With Hit and HITTS, Houston, TX, May 22, 1997, For Immediate Release, (available at http://www.tbc.com/press/pr052297.html on Jan. 28, 1999).

Texas Biotechnology Initiates Phase IIA Trial For Novel Anti–Inflammatory To Treat Asthma, Houston, TX, Oct. 22, 1997, For Immediate Release (available at http:/www.tbc.com/press/pr102297.html on Jan. 28, 1999).

Texas Biotechnology Announces Results of Phase III Clinical Study In PTCA Patients With HIT, Houston, TX, For Immediate Release, (available at http://www.tbc.com/press/pr041797.html on Jan. 29, 1999).

Texas Biotechnology's Novastan®NDA Granted Priority Review Status By The FDA, Houston, TX, Sep. 4, 1997, For Immediate Release (available at http://www.tbc.com/presspr090497.html on Jan. 28, 1999).

Texas Biotechnology Annouces Positive Data on Initial Phase IIA Asthma Study, Houston, TX, Sep. 9, 1998, For Immediate Release, (available at http://www.tbc.com/press/pr090998.html on Jan. 28, 1999).

Texas Biotechnology and Smithkline Beecham Form Alliance to Market And Develop Novastan®® (argatroban) In North American, FDA Filing for New Thrombin Inhibitor to Be Completed This Month, Houston, TX and Philadelphis, PA, Aug. 6, 1997, For Immediate Release, (available at http://www.tbc.com/press/pr080697.thml on Jan. 28, 1999).

Texas Biotechnology's Submission of Additional Novastan®Data Extends NDA Review by FDA, Houston, TX, Jan. 23, 1998, For Immediate Release (available at http://www.tbc.com/press/pr012398.html on Jan. 27, 1999).

Texas Biotechnology Updates Stockholders at 1998 Annual Meeting, Houston, TX, Jun. 9, 1998, For Immediate Release, (available at http://www.tbc.com/press/pr060998.html on Jan. 28, 1999).

Texas Biotechnology Announces Promising Clinical Updates on Phase II Trials of Novastan® In Acutte MI, Houston, TX, Mar. 17, 1997, For Immediate Release, (available at http://www.tbc.com/press/pr031797.html on Jan. 28, 1999).

Texas Biotechnology Reports Partner, Mitsubisi Chemical, Receives Stroke Indication for Novastan® In Japan, Houston, TX Jun. 18, 1996, For Immediate Release, (available at http://www.tbc.com/press/pr061896.html on Jan. 28, 1999).

Tkayama et al., Effects of recombinant human eryghropoietin on blood coagulation, fibrinolysis and endothelium in hemodyalysis patients, *Blood Purif.* *1*:53–54 (1991).

Tomita et al, "Plasma endothelin levels in patients with acute renal failure," *N. Engl. J. Med.*, 321:1127 (1989).

Vanhoutte et al., "Modulation of vascular smooth muscle contraction by the endothelium", *Annual Rev. Physiol.* *48*:307–320, (1986).

von Geldern et al., "A fluorogenic assay for endothelin–converting enzyme," *Peptide Research*, 4(1):32–35 (1991).

Warner et al., Reversal of established responses to endothelin–1 in vivo and in vitro by the endothelin receptor antagonists, BQ–123 and PD 14565, 207–213 (1994).

Weiner et al., "An all atom force field for simulations of proteins and nucleic acids," *J. Comput. Chem.*, 7(2):230–252 (1986).

Weiner et al., "A new force field for molecular mechanical simulation of nucleic acids and proteins," *J. Am. Chem. Soc.*, 106(3):765–784 (Eng.) (1984).

Williams et al., "Sarafotoxin S6c: An agonist which distinguishes between endothelin receptor subytpes," *Biochem. and Biophys. Research Commun.*, 175(2):556–561 (1991).

Wu et al., Discovery of TBC11251, a potent, long acting, orally active endothelin receptor–A selective antagonist, *J. Medicinal Chem.* *40*(*11*):1690–1697 (1997).

Wu et al., Structure–activity relationships of N–2–aryl–3–(isoxazolylsulfamoyl)–2–thiophenecarboxamides as selective endothelin receptor–A antagonists, J. Medicinal Chem. 40(11):16823–1689 (1997).

Yamashita et al., "Recombinant human erythropoietin (rHuEPO) induces high plasma endothelin (ET) levels in hemodialysis patients," *J. Am. Soc. Nephrol.*, 1:409 (1990).

Yanagisawa et al, "A novel potent vasoconstrictor peptide produced by vascular endothelial cells," *Nature*, 332:411–415 (1988).

Yanagisawa et al., The human preproendothelin–1 gene: Possible regulation by endothelial phosphoinositide turnover signaling, *J. Cardiovasc. Pharmacol.* *13*(*Suppl. 5*):S13–S17 (1989).

Yasuda et al, "Circulating immunoreactive endothelin in ischemic heart disease", *A. Heart J.* *119*:801–806, (1990).

Zamora et al, "Serum endothelin–1 concentrations and cold provocation in primary Raynaud's phenomenon", *Lancet* *336*:1144–1147, (1990).

METHOD OF TREATING GLAUCOMA

RELATED APPLICATIONS

This application is a divisional of U.S. application Ser. No. 09/441,643 to Verner et al., filed Nov. 17, 1999, entitled "THIENO-PHRIDINE SULFONAMIDES, DERIVATIVES THEREOF AND RELATED COMPOUNDS THAT MODULATE THE ACTIVITY OF ENDOTHELIN", now U.S. Pat. No. 6,329,387. U.S. application Ser. No. 09/441,643 is a continuation of U.S. application Ser. No. 09/148,643 to Verner et al., filed Sep. 4, 1998, entitled "THIENO-PYRIDINE SULFONAMIDES DERIVATIVES THEREOF AND RELATED COMPOUNDS THAT MODULATE THE ACTIVITY OF ENDOTHELIN", now U.S. Pat. No. 6,013,655. U.S. application Ser. No. 09/148,643 is a continuation of U.S. application Ser. No. 08/632,586 to Verner, filed Apr. 15, 1996, entitled "THIENO-PYRIDINE SULFONAMIDES DERIVATIVES THEREOF AND RELATED COMPOUNDS THAT MODULATE THE ACTIVITY OF ENDOTHELIN", now U.S. Pat. No. 5,804,585. The disclosures of the above applications are incorporated herein by reference in their entirety.

This application is related to U.S. application Ser. No. 09/441,643 to Verner, filed Nov. 17, 1999, entitled, "THIENO-PYRIDINE SULFONAMIDES, DERIVATIVES THEREOF AND RELATED COMPOUNDS THAT MODULATE THE ACTIVITY OF ENDOTHELIN", now U.S. Pat. No. 6,329,387; U.S. application Ser. No. 08/477,223 to Chan et al., filed Jun. 5, 1995, entitled, "THIENYL-FURYL- AND PYRROLYL SULFONAMIDES AND DERIVATIVES THEREOF THAT MODULATE THE ACTIVITY OF ENDOTHELIN", now U.S. Pat. No. 5,594,021; U.S. application Ser. No. 08/417,075 to Chan et al., filed Apr. 4, 1995, entitled, "THIENYL-, FURYL- AND PYRROLYL SULFONAMIDES AND DERIVATIVES THEREOF THAT MODULATE THE ACTIVITY OF ENDOTHELIN", now abandoned; U.S. application Ser. No. 08/416,199 to Chan et al., filed Apr. 4, 1995, entitled, "BENZENESULFONAMIDES AND THE USE THEREOF TO MODULATE THE ACTIVITY OF ENDOTHELIN", now abandoned; U.S. application Ser. No. 08/247,072 to Chan et al., filed May 20, 1994, entitled "SULFONAMIDES AND DERIVATIVES THEREOF THAT MODULATE THE ACTIVITY OF ENDOTHELIN", now U.S. Pat. No. 5,571,821; U.S. application Ser. No. 08/222,287 to Chan et al., filed Apr. 5, 1994, entitled "THIOPHENYL-, FURYL- AND PYRROLYL-SULFONAMIDES AND DERIVATIVES THEREOF THAT MODULATE THE ACTIVITY OF ENDOTHELIN", now U.S. Pat. No. 5,591,761; U.S. application Ser. No. 08/142,552 to Chan et al., filed Oct. 21, 1993, entitled "N-(4-HALO-ISOXAZOLYL)-SULFONAMIDES AND DERIVATIVES THEREOF THAT MODULATE THE ACTIVITY OF ENDOTHELIN", now U.S. Pat. No. 5,514,691; U.S. application Ser. No. 08/142,159 to Chan et al., filed Oct. 21, 1993, entitled "N-(5-ISOXAZOLYL) BIPHENYLSULFONAMIDES, N-(3-ISOXAZOLYL) BIPHENYL-SULFONAMIDES AND DERIVATIVES THEREOF THAT MODULATE THE ACTIVITY OF ENDOTHELIN", now U.S. Pat. No. 5,464,853; U.S. application Ser. No. 08/142,631 to Chan et al., filed Oct. 21, 1993, "N-(5-ISOXAZOLYL)-BENZENESULFONAMIDES, N-(3-ISOXAZOLYL)-BENZENESULFONAMIDES AND DERIVATIVES THEREOF THAT MODULATE THE ACTIVITY OF ENDOTHELIN", now abandoned; U.S. application Ser. No. 08/100,565 to Chan et al., filed Jul. 30, 1993, entitled "N-(5-ISOXAZOLYL)-SULFONAMIDES AND DERIVATIVES THEREOF THAT MODULATE THE ACTIVITY OF ENDOTHELIN", now abandoned; U.S. application Ser. No. 08/100,125 to Chan et al., filed Jul. 30, 1993, entitled "N-(3-ISOXAZOLYL)-SULFONAMIDES AND DERIVATIVES THEREOF THAT MODULATE THE ACTIVITY OF ENDOTHELIN", now abandoned; and U.S. application Ser. No. 08/065,202, to Chan, filed May 20, 1993, entitled "SULFONAMIDES AND DERIVATIVES THEREOF THAT MODULATE THE ACTIVITY OF ENDOTHELIN", now abandoned. The subject matter of each of these applications is incorporated herein in its entirety.

FIELD OF THE INVENTION

The present invention relates to the compounds that modulate the activity of the endothelin family of peptides. In particular, the invention relates to the use of sulfonamides and sulfonamide pro-drugs as endothelin agonists and antagonists.

BACKGROUND OF THE INVENTION

The vascular endothelium releases a variety of vasoactive substances, including the endothelium-derived vasoconstrictor peptide, endothelin (ET) (see, e.g., Vanhoutte et al. (1986) *Annual Rev. Physiol.* 48: 307–320; Furchgott and Zawadski (1980) *Nature* 288: 373–376). Endothelin, which was originally identified in the culture supernatant of porcine aortic endothelial cells (see, Yanagisawa et al. (1988) *Nature* 332: 411–415), is a potent twenty-one amino acid peptide vasoconstrictor. It is the most potent vasopressor known and is produced by numerous cell types, including the cells of the endothelium, trachea, kidney and brain. Endothelin is synthesized as a two hundred and three amino acid precursor preproendothelin that contains a signal sequence which is cleaved by an endogenous protease to produce a thirty-eight (human) or thirty-nine (porcine) amino acid peptide. This intermediate, referred to as big endothelin, is processed in vivo to the mature biologically active form by a putative endothelin-converting enzyme (ECE) that appears to be a metal-dependent neutral protease (see, e.g., Kashiwabara et al. (1989) *FEBS Lttrs.* 247: 337–340). Cleavage is required for induction of physiological responses (see, e.g., von Geldern et al. (1991) *Peptide Res.* 4: 32–35). In porcine aortic endothelial cells, the thirty-nine amino acid intermediate, big endothelin, is hydrolyzed at the $Trp^{21}$-$Val^{22}$ bond to generate endothelin-1 and a C-terminal fragment. A similar cleavage occurs in human cells from a thirty-eight amino acid intermediate. Three distinct endothelin isopeptides, endothelin-1, endothelin-2 and endothelin-3, that exhibit potent vasoconstrictor activity have been identified.

The family of three isopeptides endothelin-1, endothelin-2 and endothelin-3 are encoded by a family of three genes (see, Inoue et al. (1989) *Proc. Natl. Acad. Sci. USA* 86: 2863–2867; see, also Saida et al. (1989) *J. Biol. Chem.* 264: 14613–14616). The nucleotide sequences of the three human genes are highly conserved within the region encoding the mature 21 amino acid peptides and the C-terminal portions of the peptides are identical. Endothelin-2 is ($Trp^6$, $Leu^7$) endothelin-1 and endothelin-3 is ($Thr^2$, $Phe^4$, $Thr^5$, $Tyr^6$, $Lys^7$, $Tyr^{14}$) endothelin-1. These peptides are, thus, highly conserved at the C-terminal ends.

Release of endothelins from cultured endothelial cells is modulated by a variety of chemical and physical stimuli and appears to be regulated at the level of transcription and/or translation. Expression of the gene encoding endothelin-1 is increased by chemical stimuli, including adrenaline, thrombin and $Ca^{2+}$ ionophore. The production and release of endothelin from the endothelium is stimulated by angiotensin II, vasopressin, endotoxin, cyclosporine and other factors (see, Brooks et al. (1991) *Eur. J. Pharm.* 194:115–117), and is inhibited by nitric oxide. Endothelial cells appear to secrete short-lived endothelium-derived relaxing factors (EDRF), including nitric oxide or a related substance (Palmer et al. (1987) *Nature* 327: 524–526), when stimulated by vasoactive agents, such as acetylcholine and bradykinin. Endothelin-induced vasoconstriction is also attenuated by atrial natriuretic peptide (ANP).

The endothelin peptides exhibit numerous biological activities in vitro and in vivo. Endothelin provokes a strong and sustained vasoconstriction in vivo in rats and in isolated vascular smooth muscle preparations; it also provokes the release of eicosanoids and endothelium-derived relaxing factor (EDRF) from perfused vascular beds. Intravenous administration of endothelin-1 and in vitro addition to vascular and other smooth muscle tissues produce long-lasting pressor effects and contraction, respectively (see, e.g., Bolger et al. (1991) *Can. J. Physiol. Pharmacol.* 69: 406–413). In isolated vascular strips, for example, endothelin-1 is a potent ($EC_{50}=4\times10^{-10}$ M), slow acting, but persistent, contractile agent. In vivo, a single dose elevates blood pressure in about twenty to thirty minutes. Endothelin-induced vasoconstriction is not affected by antagonists to known neurotransmitters or hormonal factors, but is abolished by calcium channel antagonists. The effect of calcium channel antagonists, however, is most likely the result of inhibition of calcium influx, since calcium influx appears to be required for the long-lasting contractile response to endothelin.

Endothelin also mediates renin release, stimulates ANP release and induces a positive inotropic action in guinea pig atria. In the lung, endothelin-1 acts as a potent bronchoconstrictor (Maggi et al. (1989) *Eur. J. Pharmacol.* 160: 179–182). Endothelin increases renal vascular resistance, decreases renal blood flow, and decreases glomerular filtrate rate. It is a potent mitogen for glomerular mesangial cells and invokes the phosphoinoside cascade in such cells (Simonson et al. (1990) *J. Clin. Invest.* 85: 790–797).

There are specific high affinity binding sites (dissociation constants in the range of $2-6\times10^{-10}$ M) for the endothelins in the vascular system and in other tissues, including the intestine, heart, lungs, kidneys, spleen, adrenal glands and brain. Binding is not inhibited by catecholamines, vasoactive peptides, neurotoxins or calcium channel antagonists. Endothelin binds and interacts with receptor sites that are distinct from other autonomic receptors and voltage dependent calcium channels. Competitive binding studies indicate that there are multiple classes of receptors with different affinities for the endothelin isopeptides. The sarafotoxins, a group of peptide toxins from the venom of the snake *Atractaspis eingadensis* that cause severe coronary vasospasm in snake bite victims, have structural and functional homology to endothelin-1 and bind competitively to the same cardiac membrane receptors (Kloog et al. (1989) *Trends Pharmacol. Sci.* 10: 212–214).

Two distinct endothelin receptors, designated $ET_A$ and $ET_B$, have been identified and DNA clones encoding each receptor have been isolated (Arai et al. (1990) *Nature* 348: 730–732; Sakurai et al. (1990) *Nature* 348: 732–735). Based on the amino acid sequences of the proteins encoded by the cloned DNA, it appears that each receptor contains seven membrane spanning domains and exhibits structural similarity to G-protein-coupled membrane proteins. Messenger RNA encoding both receptors has been detected in a variety of tissues, including heart, lung, kidney and brain. The distribution of receptor subtypes is tissue specific (Martin et al. (1989) *Biochem. Biophys. Res. Commun.* 162: 130–137). $ET_A$ receptors appear to be selective for endothelin-1 and are predominant in cardiovascular tissues. $ET_B$ receptors are predominant in noncardiovascular tissues, including the central nervous system and kidney, and interact with the three endothelin isopeptides (Sakurai et al. (1990) *Nature* 348: 732–734). In addition, $ET_A$ receptors occur on vascular smooth muscle, are linked to vasoconstriction and have been associated with cardiovascular, renal and central nervous system diseases; whereas $ET_B$ receptors are located on the vascular endothelium, linked to vasodilation (Takayanagi et al. (1991) *FEBS Lttrs.* 282: 103–106) and have been associated with bronchoconstrictive disorders.

By virtue of the distribution of receptor types and the differential affinity of each isopeptide for each receptor type, the activity of the endothelin isopeptides varies in different tissues. For example, endothelin-1 inhibits $^{125}$I-labelled endothelin-1 binding in cardiovascular tissues forty to seven hundred times more potently than endothelin-3. $^{125}$I-labelled endothelin-1 binding in non-cardiovascular tissues, such as kidney, adrenal gland, and cerebellum, is inhibited to the same extent by endothelin-1 and endothelin-3, which indicates that $ET_A$ receptors predominate in cardiovascular tissues and $ET_B$ receptors predominate in non-cardiovascular tissues.

Endothelin plasma levels are elevated in certain disease states (see, e.g., International PCT Application WO 94/27979, and U.S. Pat. No. 5,382,569, which disclosures are herein incorporated in their entirety by reference). Endothelin-1 plasma levels in healthy individuals, as measured by radioimmunoassay (RIA), are about 0.26–5 pg/ml. Blood levels of endothelin-1 and its precursor, big endothelin, are elevated in shock, myocardial infarction, vasospastic angina, kidney failure and a variety of connective tissue disorders. In patients undergoing hemodialysis or kidney transplantation or suffering from cardiogenic shock, myocardial infarction or pulmonary hypertension levels as high as 35 pg/ml have been observed (see, Stewart et al. (1991) *Annals Internal Med.* 114: 464–469). Because endothelin is likely to be a local, rather than a systemic, regulating factor, it is probable that the levels of endothelin at the endothelium/smooth muscle interface are much higher than circulating levels.

Elevated levels of endothelin have also been measured in patients suffering from ischemic heart disease (Yasuda et al. (1990) *Amer. Heart J.* 119:801–806, Ray et al. (1992) *Br. Heart J.* 67:383–386). Circulating and tissue endothelin immunoreactivity is increased more than twofold in patients with advanced atherosclerosis (Lerman et al. (1991) *New Engl. J. Med.* 325:997–1001). Increased endothelin immunoreactivity has also been associated with Buerger's disease (Kanno et al. (1990) *J. Amer. Med. Assoc.* 264:2868) and Raynaud's phenomenon (Zamora et al. (1990) *Lancet* 336 1144–1147). Increased circulating endothelin levels were observed in patients who underwent percutaneous transluminal coronary angioplasty (PTCA) (Tahara et al. (1991) *Metab. Clin. Exp.* 40:1235–1237; Sanjay et al. (1991) *Circulation* 84(Suppl. 4):726), and in individuals (Miyauchi et al. (1992) *Jpn. J. Pharmacol.* 58:279P; Stewart et al. (1991) *Ann. Internal Medicine* 114:464–469) with pulmonary hypertension. Thus, there is clinical human data supporting the correlation between increased endothelin levels and numerous disease states.

Endothelin Agonists and Antagonists

Because endothelin is associated with certain disease states and is implicated in numerous physiological effects, compounds that can interfere with or potentiate endothelin-associated activities, such as endothelin-receptor interaction and vasoconstrictor activity, are of interest. Compounds that exhibit endothelin antagonistic activity have been identified. For example, a fermentation product of *Streptomyces misakiensis*, designated BE-18257B, has been identified as an $ET_A$ receptor antagonist. BE-18257B is a cyclic pentapeptide, cyclo(D-Glu-L-Ala-allo-D-Ilc-L-Leu-D-Trp), which inhibits $^{125}$I-labelled endothelin-1 binding in cardiovascular tissues in a concentration-dependent manner ($IC_{50}$ 1.4 μM in aortic smooth muscle, 0.8 μM in ventricle membranes and 0.5 μM in cultured aortic smooth muscle cells), but fails to inhibit binding to receptors in tissues in which $ET_B$ receptors predominate at concentrations up to 100 μM. Cyclic pentapeptides related to BE-18257B, such as cyclo(D-Asp-Pro-D-Val-Leu-D-TrP) (BQ-123), have been synthesized and shown to exhibit activity as $ET_A$ receptor antagonists (see, U.S. Pat. No. 5,114,918 to Ishikawa et al.; see, also, EP A1 0 436 189 to BANYU PHARMACEUTICAL CO., LTD (Oct. 7, 1991)). Studies that measure the inhibition by these cyclic peptides of endothelin-1 binding to endothelin-specific receptors indicate that these cyclic peptides bind preferentially to $ET_A$ receptors. Other peptide and non-peptidic $ET_A$ antagonists have been identified (see, e.g., U.S. Pat. Nos. 5,352,800, 5,334,598, 5,352,659, 5,248,807, 5,240,910, 5,198,548, 5,187,195, 5,082,838). These include other cyclic pentapeptides, acyltripeptides, hexapeptide analogs, certain anthraquinone derivatives, indanecarboxylic acids, certain N-pyriminylbenzenesulfonamides, certain benzenesulfonamides, and certain naphthalenesulfonamides (Nakajima et al. (1991) *J. Antibiot.* 44:1348–1356; Miyata et al. (1992) *J. Antibiot.* 45:74–8; Ishikawa et al. (1992) *J. Med. Chem.* 35:2139–2142; U.S. Pat. No. 5,114,918 to Ishikawa et al.; EP A1 0 569 193; EP A1 0 558 258; EP A1 0 436 189 to BANYU PHARMACEUTICAL CO., LTD (Oct. 7, 1991); Canadian Patent Application 2,067,288; Canadian Patent Application 2,071,193; U.S. Pat. No. 5,208,243; U.S. Pat. No. 5,270,313; U.S. Pat. No. 5,464,853; Cody et al. (1993) *Med. Chem. Res.* 3:154–162; Miyata et al. (1992) *J. Antibiot* 45:1041–1046; Miyata et al. (1992) *J. Antibiot* 45:1029–1040, Fujimoto et al. (1992) *FEBS Lett.* 305:41–44; Oshashi et al. (1002) *J. Antibiot* 45:1684–1685; EP A1 0 496 452; Clozel et al. (1993) *Nature* 365:759–761; International Patent Application WO93/08799; Nishikibe et al. (1993) *Life Sci.* 52:717–724; and Benigni et al. (1993) *Kidney Int.* 44:440–444). In general, the identified compounds have activities in in vitro assays as $ET_A$ antagonists at concentrations on the order of about 50–100 μM or less. A number of such compounds have also been shown to possess activity in in vivo animal models. Very few, if any, selective $ET_B$ antagonists have been identified.

Endothelin Antagonists and Agonists as Therapeutic Agents

It has been recognized that compounds that exhibit activity at $IC_{50}$ or $EC_{50}$ concentrations on the order of $10^{-4}$ or lower in standard in vitro assays that assess endothelin antagonist or agonist activity have pharmacological utility (see, e.g., U.S. Pat. Nos. 5,352,800, 5,334,598, 5,352,659, 5,248,807, 5,240,910, 5,198,548, 5,187,195, 5,082,838). By virtue of this activity, such compounds are considered to be useful for the treatment of hypertension such as peripheral circulatory failure, heart disease such as angina pectoris, cardiomyopathy, arteriosclerosis, myocardial infarction, pulmonary hypertension, vasospasm, vascular restenosis, Raynaud's disease, cerebral stroke such as cerebral arterial spasm, cerebral ischemia, late phase cerebral spasm after subarachnoid hemorrhage, asthma, bronchoconstriction, renal failure, particularly post-ischemic renal failure, cyclosporine nephrotoxicity such as acute renal failure, colitis, as well as other inflammatory diseases, endotoxic shock caused by or associated with endothelin, and other diseases in which endothelin has been implicated.

In view of the numerous physiological effects of endothelin and its association with certain diseases, endothelin is believed to play a critical role in these pathophysiological conditions (see, e.g., Saito et al. (1990) *Hypertension* 15: 734–738; Tomita et al. (1989) *N. Engl. J. Med.* 321: 1127; Kurihara et al. (1989) *J. Cardiovasc. Pharmacol.* 13(Suppl. 5): S13-S17; Doherty (1992) *J. Med. Chem.* 35: 1493–1508; Morel et al. (1989) *Eur. J. Pharmacol.* 167: 427–428). More detailed knowledge of the function and structure of the endothelin peptide family should provide insight in the progression and treatment of such conditions.

To aid in gaining further understanding of and to develop treatments for endothelin-mediated or related disorders, there is a need to identify compounds that modulate or alter endothelin activity. Identification of compounds that modulate endothelin activity, such as those that act as specific antagonists or agonists, may not only aid in elucidating the function of endothelin, but may yield in therapeutically useful compounds. In particular, compounds that specifically interfere with the interaction of endothelin peptides with the $ET_A$ or $ET_B$ receptors should be useful in identifying essential characteristics of endothelin peptides, should aid in the design of therapeutic agents, and may be useful as disease specific therapeutic agents.

Therefore, it is an object herein to provide compounds that have the ability to modulate the biological activity of one or more of the endothelin isopeptides. It is another object to provide compounds that have use as specific endothelin antagonists. It is also an object to use compounds that specifically interact with or inhibit the interaction of endothelin peptides with $ET_A$ or $ET_B$ receptors. Such compounds should be useful as therapeutic agents for the treatment of endothelin-mediated diseases and disorders and also for the identification of endothelin receptor subtypes.

SUMMARY OF THE INVENTION

Sulfonamides and methods for modulating the interaction of an endothelin peptide with $ET_A$ and/or $ET_B$ receptors are provided. In particular, sulfonamides and methods for inhibiting the binding of an endothelin peptide to $ET_A$ or $ET_B$ receptors are provided. The methods are effected by contacting the receptors with one or more sulfonamides prior to, simultaneously with, or subsequent to contacting the receptors with an endothelin peptide. The sulfonamides are substituted or unsubstituted monocyclic or polycyclic aromatic or heteroaromatic sulfonamides. Particularly preferred sulfonamides are N-isoxazolyl sulfonamides. More particularly preferred among such sulfonamides are those in which $Ar^2$ is a heterocycle that contains one ring, multiple rings or fused rings, typically two or three rings and one or two heteroatoms in the ring or rings.

The sulfonamides have formula I:

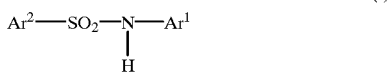

in which $Ar^1$ is a substituted or unsubstituted aryl group with one or more substituents, including an alkyl group, an aryl group, a substituted aryl group, a nitro group, an amino group or a halide or is an alkyl group. In particular, $Ar^1$ is alkyl or is a five or six membered substituted or unsubstituted aromatic or heteroaromatic ring, particularly 3 or 5-isoxazolyl and pyridazinyl, and also including thiazolyl, including 2 thiazolyl, pyrimidinyl, including 2-pyrimidinyl, or substituted benzene groups, including aryloxy substituted benzene groups or is a bicyclic or tricyclic carbon or heterocyclic ring.

$Ar^1$ is, in certain embodiments, selected from groups such as:

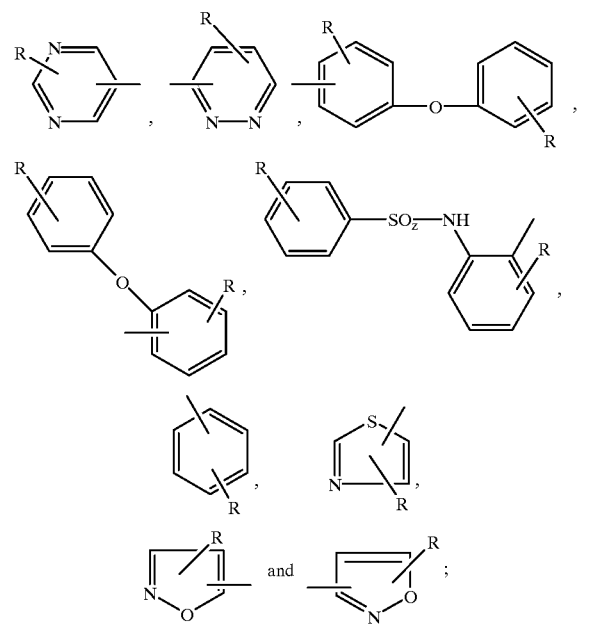

and R is selected from H, $NH_2$, halide, pseudohalide, alkyl, alkylcarbonyl, formyl, an aromatic or heteroaromatic group, alkoxyalkyl, alkylamino, alkylthio, arylcarbonyl, aryloxy, arylamino, arylthio, haloalkyl, haloaryl, carbonyl, in which the aryl and alkyl portions, are unsubstituted or substituted with any of the preceding groups, and straight or branched chains of from about 1 up to about 10–12 carbons, preferably, 1 to about 5 or 6 carbons. R is preferably H, $NH_2$, halide, $CH_3$, $CH_3O$ or another aromatic group. $Ar^2$ is any group such that the resulting sulfonamide inhibits binding by 50%, compared to binding in the absence of the sulfonamide, of an endothelin peptide to an endothelin receptor at a concentration of less than about 100 $\mu$M, except that $Ar^2$ is not phenyl or naphthyl when $Ar^1$ is N-(5-isoxazolyl) or N-(3-isoxazolyl) unless the isoxazole is a 4-halo-isoxazole, a 4-higher alkyl ($C_8$ to $C_{15}$)-isoxazole, or the compound is a 4-biphenyl that is unsubstituted at the 2 or 5 position on the sulfonamide-linked phenyl group.

$Ar^2$ is any group such that the resulting sulfonamide inhibits binding by 50%, compared to binding in the absence of the sulfonamide, of an endothelin peptide to an endothelin receptor at a concentration of less than about 100 $\mu$M, with the above proviso. In particular, $Ar^2$ is a substituted or unsubstituted group selected from among groups including, but not limited to, the following: naphthyl, phenyl, biphenyl, quinolyl, styryl, thienyl, furyl, isoquinolyl, pyrrolyl, benzofuranyl, pyridinyl, thionaphthalyl, indolyl, alkyl, alkenyl, pyridinyl, and other single and fused ring heterocyclic groups. It is understood that the positions indicated for substituents, including the sulfonamide groups, may be varied. Thus, for example, compounds herein encompass groups that include thiophene-3-sulfonamides and thiophene-2-sulfonamides.

In certain embodiments described in detail herein, $Ar^2$ is a single ring heterocycle, particularly a 5-membered ring, or is a fused bicyclic or tricyclic heterocycle that contains one or more, particularly one, heteroatom selected from S, O, N and $NR^{11}$, in the ring, where $R^{11}$ contains up to about 30 carbon atoms, preferably 1 to 10, more preferably 1 to 6 and is selected from hydrogen, alkyl, alkenyl, alkynyl, aryl, alkylaryl, heterocycle, aralkyl, aralkoxy, cycloalkyl, cycloalkenyl, cycloalkynyl, $C(O)R^{15}$ and $S(O)_nR^{15}$ in which n is 0–2; $R^{15}$ is hydrogen, alkyl, alkenyl, alkynyl, aryl, alkylaryl, heterocycle, aralkyl, aralkoxy, cycloalkyl, cycloalkenyl, cycloalkynyl; $R^{11}$ and $R^{15}$ are unsubstituted or are substituted with one or more substituents each selected independently from Z, which is hydrogen, halide, pseudohalide, alkyl, alkoxy, alkenyl, alkynyl, aryl, heterocycle, aralkyl, aralkoxy, cycloalkyl, cycloalkenyl, cycloalkynyl, OH, ON, $C(O)R^{16}$, $CO_2R^{16}$, SH, $S(O)_nR^{16}$ in which n is 0–2, NHOH, $NR^{12}R^{16}$, $NO_2$, $N_3$, $OR^{16}$, $R^{12}NCOR^{16}$ and $CONR^{12}R^{16}$; $R^{16}$ is hydrogen, alkyl, alkenyl, alkynyl, aryl, alkylaryl, heterocycle, aralkyl, aralkoxy, cycloalkyl, cycloalkenyl or cycloalkynyl; $R^{12}$, which is selected independently from $R^{11}$ and Z, is selected from hydrogen, alkyl, alkenyl, alkynyl, aryl, alkylaryl, heterocycle, aralkyl, aralkoxy, cycloalkyl, cycloalkenyl, cycloalkynyl, $C(O)R^{17}$ and $S(O)_nR^{17}$ in which n is 0–2; and $R^{17}$ is hydrogen, alkyl, alkenyl, alkynyl, aryl, alkylaryl, heterocycle, aralkyl, aralkoxy, cycloalkyl, cycloalkenyl or cycloalkynyl; each of $R^{11}$, $R^{12}$, $R^{15}$ and $R^{16}$ may be further substituted with the any of the groups set forth for Z.

In certain preferred embodiments herein, $R^{11}$ is aryl, such as phenyl or alkyl phenyl, hydrogen or lower alkyl.

In the embodiments described in detail herein, $Ar^2$ is a fused ring bicyclic heterocycle and $Ar^1$ is preferably a five or 6-membered heterocyclic ring. $Ar^1$ is preferably an isoxazole and $Ar^2$ is preferably a fused ring bicyclic heterocycle containing one heteroatom in each ring and containing 5 or 6 members in each ring.

In particular, $Ar^2$ is selected from among fused bicyclic heteroaryl groups, such as those having formula:

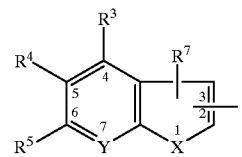

in which Y is N or $O^+$, preferably N; X is S, O, $NR^{11}$, which is as defined above, $R^3$, $R^4$ and $R^5$ are selected from (i), (ii), (iii) or (iv):
(i) $R^3$, $R^4$ and $R^5$ are each selected independently from among H, NHOH, $NH_2$, $NO_2$, $N_3$, halide, pseudohalide, alkyl, alkenyl, alkynyl, alkenyl, alkylaryl, aryloxy, aryl, heteroaryl, alkoxy, alkylamino, alkylthio, alkoxyalkyl, alkylsulfinyl, alkylsulfonyl, aryloxy, arylamino, arylthio, arylsulfinyl, arylsulfonyl, haloalkyl, haloaryl, alkoxycarbonyl, alkylcarbonyl, arylcarbonyl, formyl, amido, where the alkyl, alkenyl, alkynyl portions are straight or branched chains of from about 1 up to about 10 carbons, preferably, 1 to about 5 or 6 carbons and the aryl portions contain from 3 up to about 10 carbons, preferably 6 carbons; or, alternatively, (ii) two of $R^3$, $R^4$ and $R^5$ together are substituted or unsubstituted 1,3-butadienyl, 4-dimethylamino-1,3 butadienyl, 1-chloro-1,3-butadiene, 1-aza-1,3-butadienyl or 2-aza-1,3-butadienyl groups or form alkylenedioxy; and the others of $R^3$, $R^4$ and $R^5$ are as defined in (i) above or also form substituted or unsubstituted 1,3-butadienyl, 4-dimethylamino-1,3 butadiene, 1-chloro-1,3-butadienyl, 1-aza-1,3-butadienyl or 2-aza-1,3-butadienyl groups or form alkylenedioxy; or alternatively, (iii) two of $R^3$, $R^4$ and $R^5$ are independently selected from alkyl, alkoxy, halide aminoalkyl, dialkylaminoalkyl, in which the alkyl and alkoxy groups contain from 1 to 10, preferably 1 to 6 carbons, and are straight or branched chains and the others are H; or (iv) any two of $R^3$, $R^4$ and $R^5$, which are each selected as in (i) form fused carbocyclic or heterocyclic rings; and $R^7$ is hydrogen or contains up to about 50 carbon atoms, generally up to about 30, more generally 20 or fewer, and is selected from hydrogen, halide, pseudohalide, alkyl, alkoxy, alkenyl, alkynyl, aryl, aryloxy, heterocycle, aralkyl, aralkoxy, cycloalkyl, cycloalkenyl, cycloalkynyl, OH, CN, SH, $(CH_2)_rR^{18}$, $C(O)R^{18}$, $CO_2R^{18}$, $(CH_2)_rR^{18}$, $(CH_2)_rCOR^{18}$ $(CH_2)_r$ $CO(CH_2)_sR^{18}$, $OR^{18}$, $S(O)_nR^{18}$ in which n is 0–2, and r and s are each independently 0 to 6, preferably 1–3, HNOH, $NR^{18}R^{19}$, $NO_2$, $N_3$, $OR^{18}$, $R^{19}NCOR^{18}$ and $CONR^{19}R^{18}$, in which $R^{19}$ is selected from hydrogen, alkyl, alkenyl, alkynyl, aryl, alkylaryl, alkoxy, aryloxy, heterocycle, aralkyl, aralkoxy, cycloalkyl, cycloalkenyl, cycloalkynyl, $C(O)R^{20}$, $S(O)_nR^{20}$ in which n is 0–2; and $R^{18}$ and $R^{20}$ are independently selected from hydrogen, alkyl, alkenyl, alkynyl, aryl, alkylaryl, heterocycle, alkoxy, aryloxy, aralkyl, aralkoxy, cycloalkyl, cycloalkenyl or cycloalkynyl; and any of the groups set forth for $R^7$ is unsubstituted or substituted with any substituents set forth for Z, which is hydrogen, halide, pseudohalide, alkyl, alkoxy, alkenyl, alkynyl, aryl, aryloxy, heterocycle, aralkyl, aralkoxy, cycloalkyl, cycloalkenyl, cycloalkynyl, OH, ON, $C(O)R^{21}$, $CO_2R^{21}$, SH, $S(O)_nR^{21}$ in which n is 0–2, NHOH, $NR^{22}R^{21}$, $NO_2$, $N_3$, $OR^{21}$, $R^{22}NCOR^{21}$ and $CONR^{22}R^{21}$; $R^{22}$ is selected from hydrogen, alkyl, alkenyl, alkynyl, aryl, alkylaryl, heterocycle, aralkyl, alkoxy, aralkoxy, cycloalkyl, cycloalkenyl, cycloalkynyl, $C(O)R^{23}$ and $S(O)_nR^{23}$ in which n is 0–2; and $R^{21}$ and $R^{23}$ are independently selected from hydrogen, alkyl, alkenyl, alkynyl, aryl, alkylaryl, heterocycle, aralkyl, aralkoxy, cycloalkyl, cycloalkenyl or cycloalkynyl, and $R^{14}$ is absent.

In more preferred embodiments $Ar^1$ is an isoxazole and the compounds are represented by the formulae II:

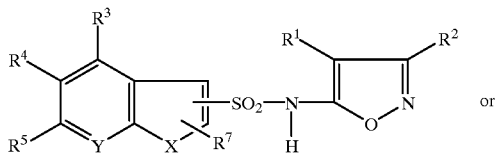

or

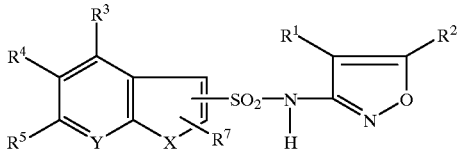

in which Y is N or $O^+$, preferably N; X is S, O, $NR^{11}$, which is as defined above, and is preferably hydrogen or aryl, more preferably hydrogen or phenyl; and $R^1$ and $R^2$ are either (i), (ii) or (iii) as follows:

(i) $R^1$ and $R^2$ are each independently selected from H, $NH_2$, $NO_2$, halide, pseudohalide, alkyl, alkenyl, alkynyl, aryl, arylalkyl, heteroaryl, alkoxy, alkylamino, alkylthio, alkyloxy, haloalkyl, alkylsufinyl, alkylsulfonyl, aryloxy, arylamino, arylthio, arylsufinyl, arylsulfonyl, haloalkyl, haloaryl, alkoxycarbonyl, alkylcarbonyl, aminocarbonyl, arylcarbonyl, formyl, substituted or unsubstituted amido, substituted or unsubstituted ureido, in which the alkyl, alkenyl and alkynyl portions contain from 1 up to about 14 carbon atoms and are either straight or branched chains or cyclic, and the aryl portions contain from about 4 to about 16 carbons, except that $R^2$ is not halide or pseudohalide; or, (ii) $R^1$ and $R^2$ together form $—(CH_2)_n$, where n is 3 to 6; or (iii) $R^1$ and $R^2$ together form 1,3-butadienyl.

In preferred embodiments $R^7$ is $(CH_2)_rR^{18}$, where $R^{18}$ is aryl, preferably phenyl or pyrimidinyl, more preferably phenyl, which is unsubstituted or substituted with alkyl, haloalkyl, halide, or such that two adjacent positions are substituted and together form alkylenedioxy, particularly methylenedioxy and ethylenedioxy.

In all preferred embodiments herein, $R^1$ and $R^2$ are each selected independently from among alkyl, lower alkenyl, lower alkynyl, lower haloalkyl, halide, pseudohalide or H, except that $R^2$ is not halide.

In the embodiments provided herein, the alkyl, alkynyl and alkenyl portions of each listed substituent are straight or branched chains, acyclic or cyclic, and preferably have from about 1 up to about 10 carbons; in more preferred embodiments they have from 1–6 carbons. The aryl, alicyclic, aromatic rings and heterocyclic groups can have from 3 to 16, generally, 3–7, more often 5–7 members in the rings, and may be single or fused rings. The ring size and carbon chain length are selected up to an amount that the resulting molecule binds and retains activity as an endothelin antagonist or agonist, such that the resulting compound inhibits binding by 50%, compared to binding in the absence of the sulfonamide, of an endothelin peptide to an endothelin receptor at a concentration of less than about 100 μM.

In the preferred compounds herein, $R^2$ is preferably, selected from among alkyl, lower alkenyl, lower alkynyl, lower haloalkyl, or H; and $R^1$ is halide or lower alkyl, and more preferably, $R^1$ is bromide or chloride, methyl or ethyl and $R^2$ is methyl, ethyl or haloalkyl, particularly $CF_3$. In the most active compounds provided herein, as evidenced by in vitro binding assays, $R^1$ is bromide or chloride.

In other preferred compounds $R^{10}$ is $C(O)R^{27}$ in which $R^{27}$ is aryl, and is preferably $(CH_2)_rC(O)(CH_2)_p$-aryl, $(CH_2)_rC(O)$aryl, $(CH_2)_rS(O)_q(CH_2)_p$-aryl, $C(O)NR^{11}$-aryl, $NHC(O)(CH_2)_r$-aryl, $NR^{11}$-aryl, $(CH_2)_r$aryl in which p and r are each independently selected from 0–10, preferably 0–6, more preferably 0–3, most preferably 0 or 1 and q is 0–3, preferably 0–2. The aryl portion is unsubstituted or is substituted with groups such as alkyl, alkoxy, alkoxyalkyl, halogen, alkylenedioxy, particularly methylene dioxy, N-alkyl, N-alkyoxy, amino, nitro and other such groups. The alkyl substituents are preferably lower alkyl, more preferably containing 1–3 carbons.

Of the compounds described herein, those that inhibit or increase an endothelin-mediated activity by about 50% at concentrations of less than about 10 μM are preferred. More preferred are those that inhibit or increase an endothelin-mediated activity by about 50% at concentrations of less than about 1 μM, more preferably less than about 0.1 μM, even more preferably less than about 0.01 μM, and most preferably less than about 0.005 μM. It is noted that, as described below, the $IC_{50}$ concentration determined in the in vitro assays is a non-linear function of incubation temperature. The preferred values recited herein refer to the assays that are performed at 4° C. When the assays are performed at 24° C., somewhat higher (see, Table 1) $IC_{50}$ concentrations are observed. Accordingly, the preferred $IC_{50}$ concentrations are about 10-fold higher.

Also among me most preferred compounds for use in methods provided herein, are those that are $ET_A$ selective, i.e., they interact with $ET_A$ receptors at substantially lower concentrations (at an $IC_{50}$ at least about 10-fold lower, preferably 100-fold lower) than they interact with $ET_B$ receptors. In particular, compounds that interact with $ET_A$ with an $IC_{50}$ of less than about 10 μM, preferably less than 1 μM, more preferably less than 0.1 μM, but with $ET_B$ with an $IC_{50}$ of greater than about 10 μM or compounds that interact with $ET_B$ with an $IC_{50}$ of less than about 10 μM, preferably less than 1 μM, more preferably less than 0.1 μM, but with $ET_A$ with an $IC_{50}$ of greater than about 10 μM are preferred.

Preferred compounds also include compounds that are $ET_B$ receptor selective or that bind to $ET_B$ receptors with an $IC_{50}$ of less than about 1 μM. $ET_B$ selective compounds interact with $ET_B$ receptors at $IC_{50}$ concentrations that are at least about 10-fold lower than the concentrations at which they interact with $ET_A$ receptors. In these compounds, $R^2$ is selected from among alkyl, lower alkenyl, lower alkynyl, lower haloalkyl, halide or H; and $R^1$ is halide or lower alkyl, and in preferred embodiments, $R^1$ is bromide or chloride; $R^9$ and $R^{10}$ are selected independently from hydrogen, lower alkyl, preferably methyl or ethyl, or halide, and $R^8$, which is the substituent at the 5-position (see, e.g., formulae III and IV), is aryl or a heterocycle, particularly phenyl and isoxazolyl, which are unsubstituted or substituted with Z, which is preferably lower alkyl or halide.

Pharmaceutical compositions formulated for administration by an appropriate route and means containing effective concentrations of one or more of the compounds provided herein or pharmaceutically acceptable salts or acids thereof that deliver amounts effective for the treatment of hypertension, stroke, asthma, shock, ocular hypertension, glaucoma, renal failure, inadequate retinal perfusion and other conditions that are in some manner mediated by an endothelin peptide or that involve vasoconstriction or whose symptoms can be ameliorated by administration of an endothelin antagonist or agonist, are also provided. Particularly preferred compositions are those that deliver amounts effective for the treatment of hypertension or renal failure. The effective amounts and concentrations are effective for ameliorating any of the symptoms of any of the disorders.

Methods for inhibiting binding of an endothelin peptide to an endothelin receptor are provided. These methods are practiced by contacting the receptor with one or more of the compounds provided herein simultaneously, prior to, or subsequent to contacting the receptor with an endothelin peptide.

Methods for treatment of endothelin-mediated disorders, including but not limited to, hypertension, asthma, shock, ocular hypertension, glaucoma, inadequate retinal perfusion and other conditions that are in some manner mediated by an endothelin peptide, or for treatment of disorder that involve vasoconstriction or that are ameliorated by administration of an endothelin antagonist or agonist are provided.

In particular, methods of treating endothelin-mediated disorders by administering effective amounts of the sulfonamides, prodrugs or other suitable derivatives of the sulfonamides are provided. In particular, methods for treating endothelin-mediated disorders, including hypertension, cardiovascular diseases, cardiac diseases including myocardial infarction, pulmonary hypertension, erythropoietin-mediated hypertension, respiratory diseases and inflammatory diseases, including asthma, bronchoconstriction, ophthalmologic diseases, gastroenteric diseases, renal failure, endotoxin shock, menstrual disorders, obstetric conditions, wounds, anaphylactic shock, hemorrhagic shock, and other diseases in which endothelin mediated physiological responses are implicated, by administering effective amounts of one or more of the compounds provided herein in pharmaceutically acceptable carriers are provided. Preferred methods of treatment are methods for treatment of hypertension and renal failure.

More preferred methods of treatment are those in which the compositions contain at least one compound that inhibits the interaction of endothelin-1 with $ET_A$ receptors at an $IC_{50}$ of less than about 10 μM, and preferably less than about 5 μM, more preferably less than about 1 μM, even more preferably less than 0.1 μM, and most preferably less than 0.05 μM Other preferred methods are those in which the compositions contain one or more compounds that is (are) $ET_A$ selective or one or more compounds that is (are) $ET_B$ selective. Methods in which the compounds are $ET_A$ selective are for treatment of disorders, such as hypertension; and methods in which the compounds are $ET_B$ selective are for treatment of disorders, such as asthma, that require bronchodilation.

In practicing the methods, effective amounts of compositions containing therapeutically effective concentrations of the compounds formulated for oral, intravenous, local and topical application for the treatment of hypertension, cardiovascular diseases, cardiac diseases, including myocardial infarction, respiratory diseases, including asthma, inflammatory diseases, ophthalmologic diseases, gastroenteric diseases, renal failure, immunosuppressant-mediated renal vasoconstriction, erythropoietin-mediated vasoconstriction, endotoxin shock, anaphylactic shock, hemorrhagic shock, pulmonary hypertension, and other diseases in which endothelin mediated physiological responses are implicated are administered to an individual exhibiting the symptoms of one or more of these disorders. The amounts are effective to ameliorate or eliminate one or more symptoms of the disorders.

Methods for the identification and isolation of endothelin receptor subtypes are also provided. In particular, methods for detecting, distinguishing and isolating endothelin receptors using the disclosed compounds are provided. In particular, methods are provided for detecting, distinguishing and isolating endothelin receptors using the compounds provided herein.

In addition, methods for identifying compounds that are suitable for use in treating particular diseases based on their preferential affinity for a particular endothelin receptor subtype are also provided.

Articles of manufacture containing packaging material, a compound provided herein, which is effective for ameliorating the symptoms of an endothelin-mediated disorder, antagonizing the effects of endothelin or inhibiting binding of an endothelin peptide to an ET receptor with an $IC_{50}$ of less than about 10 µM, within the packaging material, and a label that indicates that the compound or salt thereof is used for antagonizing the effects of endothelin, treating an endothelin-mediated disorder, or inhibiting the binding of an endothelin peptide to an ET receptor are provided.

DETAILED DESCRIPTION OF PREFERRED EMBODIMENTS

Definitions

Unless defined otherwise, all technical and scientific terms used herein have the same meaning as is commonly understood by one of skill in the art to which this invention belongs. All patents and publications referred to herein are incorporated by reference.

As used herein, endothelin (ET) peptides include peptides that have substantially the amino acid sequence of endothelin-1, endothelin-2 or endothelin-3 and that act as potent endogenous vasoconstrictor peptides.

As used herein, an endothelin-mediated condition is a condition that is caused by abnormal endothelin activity or one in which compounds that inhibit endothelin activity have therapeutic use. Such diseases include, but are not limited to hypertension, cardiovascular disease, asthma, inflammatory diseases, ophthalmologic disease, menstrual disorders, obstetric conditions, gastroenteric disease, renal failure, pulmonary hypertension, endotoxin shock, anaphylactic shock, or hemorrhagic shock. Endothelin-mediated conditions also include conditions that result from therapy with agents, such as erythropoietin and immunosuppressants, that elevate endothelin levels.

As used herein an effective amount of a compound for treating a particular disease is an amount that is sufficient to ameliorate, or in some manner reduce the symptoms associated with the disease. Such amount may be administered as a single dosage or may be administered according to a regimen, whereby it is effective. The amount may cure the disease but, typically, is administered in order to ameliorate the symptoms of the disease. Typically, repeated administration is required to achieve the desired amelioration of symptoms.

As used herein, an endothelin agonist is a compound that potentiates or exhibits a biological activity associated with or possessed by an endothelin peptide.

As used herein, an endothelin antagonist is a compound, such as a drug or an antibody, that inhibits endothelin-stimulated vasoconstriction and contraction and other endothelin-mediated physiological responses. The antagonist may act by interfering with the interaction of the endothelin with an endothelin-specific receptor or by interfering with the physiological response to or bioactivity of an endothelin isopeptide, such as vasoconstriction. Thus, as used herein, an endothelin antagonist interferes with endothelin-stimulated vasoconstriction or other response or interferes with the interaction of an endothelin with an endothelin-specific receptor, such as $ET_A$ receptors, as assessed by assays known to those of skill in the art.

The effectiveness of potential agonists and antagonists can be assessed using methods known to those of skill in the art. For example, endothelin agonist activity can be identified by its ability to stimulate vasoconstriction of isolated rat thoracic aorta or portal vein ring segments (Borges et al. (1989) "Tissue selectivity of endothelin" *Eur. J. Pharmacol.* 165: 223–230). Endothelin antagonist activity can be assessed by the ability to interfere with endothelin-induced vasoconstriction. Exemplary assays are set forth in the EXAMPLES. As noted above, the preferred $IC_{50}$ concentration ranges are set forth with reference to assays in which the test compound is incubated with the ET receptor-bearing cells at 4° C. Data presented for assays in which the incubation step is performed at the less preferred 24° C. are identified. It is understood that for purposes of comparison, these concentrations are somewhat higher than the concentrations determined at 4° C.

As used herein, the biological activity or bioactivity of endothelin includes any activity induced, potentiated or influenced by endothelin in vivo. It also includes the ability to bind to particular receptors and to induce a functional response, such as vasoconstriction. It may be assessed by in vivo assays or by in vitro assays, such as those exemplified herein. The relevant activities include, but are not limited to, vasoconstriction, vasorelaxation and bronchodilation. For example, $ET_B$ receptors appear to be expressed in vascular endothelial cells and may mediate vasodilation and other such responses; whereas $ET_A$ receptors, which are endothelin-1-specific, occur on smooth muscle and are linked to vasoconstriction. Any assay known to those of skill in the art to measure or detect such activity may be used to assess such activity (see, e.g., Spokes et al. (1989) *J. Cardiovasc. Pharmacol.* 13 (Suppl. 5):S191-S192; Spinella et al. (1991) *Proc. Natl. Acad. Sci. USA* 88: 7443–7446; Cardell et al. (1991) *Neurochem. Int.* 18:571–574); and the Examples herein).

As used herein, the $IC_{50}$ refers to an amount, concentration or dosage of a particular test compound that achieves a 50% inhibition of a maximal response, such as binding of endothelin to tissue receptors, in an assay that measures such response.

As used herein, $EC_{50}$ refers to a dosage, concentration or amount of a particular test compound that elicits a dose-dependent response at 50% of maximal expression of a particular response that is induced, provoked or potentiated by the particular test compound.

As used herein, a sulfonamide that is $ET_A$ selective refers to sulfonamides that exhibit an $IC_{50}$ that is at least about 10-fold lower with respect to $ET_A$ receptors than $ET_B$ receptors.

As used herein, a sulfonamide that is $ET_B$ selective refers to sulfonamides that exhibit an $IC_{50}$ that is at least about 10-fold lower with respect to $ET_B$ receptors than $ET_A$ receptors.

As used herein, pharmaceutically acceptable salts, esters or other derivatives of the compounds include any salts, esters or derivatives that may be readily prepared by those of skill in this art using known methods for such derivatization and that produce compounds that may be administered to animals or humans without substantial toxic effects and that either are pharmaceutically active or are prodrugs. For example, hydroxy groups can be esterified or etherified.

As used herein, treatment means any manner in which the symptoms of a conditions, disorder or disease are ameliorated or otherwise beneficially altered. Treatment also encompasses any pharmaceutical use of the compositions herein, such as use as contraceptive agents.

As used herein, amelioration of the symptoms of a particular disorder by administration of a particular pharmaceutical composition refers to any lessening, whether permanent or temporary, lasting or transient that can be attributed to or associated with administration of the composition.

As used herein, substantially pure means sufficiently homogeneous to appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

As used herein, biological activity refers to the in vivo activities of a compound or physiological responses that result upon in vivo administration of a compound, composition or other mixture. Biological activity, thus, encompasses therapeutic effects and pharmaceutical activity of such compounds, compositions and mixtures.

As used herein, a prodrug is a compound that, upon in vivo administration, is metabolized or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) *Medicinal Chemistry A Biochemical Approach*, Oxford University Press, New York, pages 388–392). For example, succinylsulfathiazole is a prodrug of 4-amino-N-(2-thiazolyl) benzenesulfonamide (sulfathiazole) that exhibits altered transport characteristics.

As used herein, "halogen" or "halide" refers to F, Cl, Br or I.

As used herein, pseudohalides are compounds that behave substantially similar to halides. Such compounds can be used in the same manner and treated in the same manner as halides (X$^-$, in which X is a halogen, such as Cl or Br). Pseudohalides include, but are not limited to cyanide, cyanate, thiocyanate, selenocyanate and azide.

As used herein, lower alkyl, lower alkenyl, and lower alkynyl refer to carbon chains having less than about 6 carbons. In preferred embodiments of the compounds provided herein that include alkyl, alkenyl, or alkynyl portions include lower alkyl, lower alkenyl, and lower alkynyl portions.

As used herein aryl refers to cyclic groups containing from 3 to 15 or 16 carbon atoms, preferably from 5 to 10. Aryl groups include, but are not limited to groups, such as phenyl, substituted phenyl, naphthyl, substituted naphthyl, in which the substituent is lower alkyl, halogen, or lower alkoxy. Preferred aryl groups are lower aryl groups that contain less than 7 carbons in the ring structure.

As used herein, the nomenclature alkyl, alkoxy, carbonyl, etc. are used as is generally understood by those of skill in this art. For example, as used herein alkyl refers to saturated carbon chains that contain one or more carbons; the chains may be straight or branched or include cyclic portions or be cyclic. As used herein, alicyclic refers to aryl groups that are cyclic.

As used herein, "haloalkyl" refers to a lower alkyl radical in which one or more of the hydrogen atoms are replaced by halogen including, but not limited to, chloromethyl, trifluoromethyl, 1-chloro-2-fluoroethyl and the like.

As used herein, "haloalkoxy" refers to RO— in which R is a haloalkyl group.

As used herein, "aminocarbonyl" refers to —C(O)NH$_2$.

As used herein, "alkylaminocarbonyl" refers to —C(O)NHR in which R is hydrogen, alkyl, preferably lower alkyl or aryl, preferably lower aryl. As used herein "dialkylaminocarbonyl" as used herein refers to —C(O)NR'R in which R' and R are independently selected from alkyl or aryl, preferably lower alkyl or lower aryl; "carboxamide" refers to groups of formula NR'COR.

As used herein, "alkoxycarbonyl" as used herein refers to —C(O)OR in which R is alkyl, preferably lower alkyl or aryl, preferably lower aryl.

As used herein, "alkoxy" and "thioalkoxy" refer to RO— and RS—, in which R is alkyl, preferably lower alkyl or aryl, preferably lower aryl.

As used herein, "haloalkoxy" refers to RO— in which R is a haloalkyl group.

As used herein, "aminocarbonyl" refers to —C(O)NH$_2$.

As used herein, "alkylaminocarbonyl" refers to —C(O)NHR in which R is alkyl, preferably lower alkyl or aryl, preferably lower aryl.

As used herein, "alkoxycarbonyl" refers to —C(O)OR in which R is alkyl, preferably lower alkyl.

As used herein, cycloalkyl refers to saturated cyclic carbon chains; cycloalkyenyl and cycloalkynyl refer to cyclic carbon chains that include at least one unsaturated triple bond. The cyclic portions of the carbon chains may include one ring or two or more fused rings.

As used herein, heterocycle or heteroaryl refers to ring structures that include at least one carbon atom and one or more atoms, such as N, S and O. The rings may be single rings or two or more fused rings. Heteroaryl is used interchangeable with heterocycle.

As used herein, any corresponding N-(4-halo-3-methyl-5-isoxazolyl), N-(4-halo-5-methyl-3-isoxazolyl), N-(3,4-dimethyl-5-isoxazolyl), N-(4-halo-5-methyl-3-isoxazolyl), N-(4-halo-3-methyl-5-isoxazolyl), N-(4,5-dimethyl-3-isoxazolyl) derivative thereof refers to compounds in which Ar$^2$ is the same as the compound specifically set forth, but Ar$^1$ is N-(4-halo-3-methyl-5-isoxazolyl), N-(4-halo-5-methyl-3-isoxazolyl), N-(3,4-dimethyl-5-isoxazolyl), N-(4-halo-5-methyl-3-isoxazolyl), N-(4-halo-3-methyl-5-isoxazolyl), or N-(4,5-dimethyl-3-isoxazolyl) in which halo is any halide, preferably Cl or Br.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:942–944).

A Compounds for Use in Treating Endothelin-Mediated Diseases

Compounds and methods for treating endothelin-mediated diseases using the compounds of formula I are provided. In particular, the compounds provided herein have formulae II:

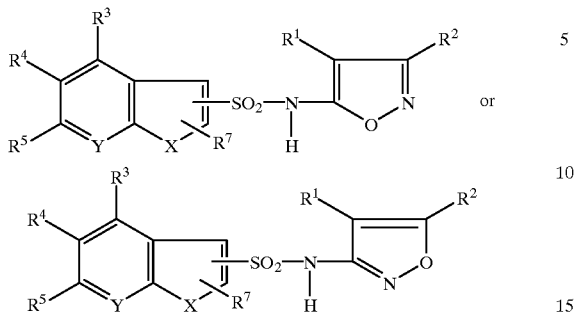

in which Y is N or O$^+$; X is S, O, NR$^{11}$, in which R$^{11}$ contains up to about 30 carbon atoms, preferably 1 to 10, more preferably 1 to 6 and is selected from hydrogen, alkyl, alkenyl, alkynyl, aryl, alkylaryl, heterocycle, aralkyl, aralkoxy, cycloalkyl, cycloalkenyl, cycloalkynyl, C(O)R$^{15}$ and S(O)$_n$R$^{15}$ in which n is 0–2; R$^{15}$ is hydrogen, alkyl, alkenyl, alkynyl, aryl, alkylaryl, heterocycle, aralkyl, aralkoxy, cycloalkyl, cycloalkenyl, cycloalkynyl; R$^{11}$ and R$^{15}$ are unsubstituted or are substituted with one or more substituents each selected independently from Z, which is hydrogen, halide, pseudohalide, alkyl, alkoxy, alkenyl, alkynyl, aryl, heterocycle, aralkyl, aralkoxy, cycloalkyl, cycloalkenyl, cycloalkynyl, OH, CN, C(O)R$^{16}$, CO$_2$R$^{16}$, SH, S(O)$_n$R$^{16}$ in which n is 0–2, NHOH, NR$^{12}$R$^{16}$, NO$_2$, N$_3$, OR$^{16}$, R$^{12}$NCOR$^{16}$ and CONR$^{12}$R$^{16}$; R$^{16}$ is hydrogen, alkyl, alkenyl, alkynyl, aryl, alkylaryl, heterocycle, aralkyl, aralkoxy, cycloalkyl, cycloalkenyl or cycloalkynyl; R$^{12}$, which is selected independently from R$^{11}$ and Z, is selected from hydrogen, alkyl, alkenyl, alkynyl, aryl, alkylaryl, heterocycle, aralkyl, aralkoxy, cycloalkyl, cycloalkenyl, cycloalkynyl, C(O)R$^{17}$ and S(O)$_n$R$^{17}$ in which n is 0–2; and R$^{17}$ is hydrogen, alkyl, alkenyl, alkynyl, aryl, alkylaryl, heterocycle, aralkyl, aralkoxy, cycloalkyl, cycloalkenyl or cycloalkynyl; each of R$^{11}$, R$^{12}$, R$^{15}$ and R$^{16}$ may be further substituted with the any of the groups set forth for Z; R$^1$ and R$^2$ are either (i), (ii) or (iii) as follows:
  (i) R$^1$ and R$^2$ are each independently selected from H, NH$_2$, NO$_2$, halide, pseudohalide, alkyl, alkenyl, alkynyl, aryl, arylalkyl, heteroaryl, alkoxy, alkylamino, alkylthio, alkyloxy, haloalkyl, alkylsufinyl, alkylsulfonyl, aryloxy, arylamino, arylthio, arylsufinyl, arylsulfonyl, haloalkyl, haloaryl, alkoxycarbonyl, alkylcarbonyl, aminocarbonyl, arylcarbonyl, formyl, substituted or unsubstituted amido, substituted or unsubstituted ureido, in which the alkyl, alkenyl and alkynyl portions contain from 1 up to about 14 carbon atoms and are either straight or branched chains or cyclic, and the aryl portions contain from about 4 to about 16 carbons, except that R$^2$ is not halide or pseudohalide; or,
  (ii) R$^1$ and R$^2$ together form —(CH$_2$)$_n$, where n is 3 to 6; or,
  (iii) R$^1$ and R$^2$ together form 1,3-butadienyl;
R$^3$, R$^4$ and R$^5$ are selected from (i), (ii), (iii) or (iv):
  (i) R$^3$, R$^4$ and R$^5$ are each selected independently from among H, NHOH, NH$_2$, NO$_2$, N$_3$, halide, pseudohalide, alkyl, alkenyl, alkynyl, alkenyl, alkylaryl, aryloxy, aryl, heteroaryl, alkoxy, alkylamino, alkylthio, alkoxyalkyl, alkylsulfinyl, alkylsulfonyl, aryloxy, arylamino, arylthio, arylsulfinyl, arylsulfonyl, haloalkyl, haloaryl, alkoxycarbonyl, alkylcarbonyl, arylcarbonyl, formyl, amido, where the alkyl, alkenyl, alkynyl portions are straight or branched chains of from about 1 up to about 10 carbons, preferably, 1 to about 5 or 6 carbons and the aryl portions contain from 3 up to about 10 carbons, preferably 6 carbons; or, alternatively,
  (ii) two of R$^3$, R$^4$ and R$^5$ together are substituted or unsubstituted 1,3-butadienyl, 4-dimethylamino-1,3 butadienyl, 1-chloro-1,3-butadienyl, 1-aza-1,3-butadienyl or 2-aza-1,3-butadienyl groups; and the others of R$^3$, R$^4$ and R$^5$ are as defined in (i) above; or alternatively,
  (iii) R$^4$ is H; and R$^3$ and R$^5$ are each independently selected from alkyl, alkoxy, halide aminoalkyl, dialkylaminoalkyl, in which the alkyl and alkoxy groups contain from 1 to 10, preferably 1 to 6 carbons, and are straight or branched chains; or
  (iv) any two of R$^3$, R$^4$ and R$^5$, which are each selected as in (i) form fused carbocyclic or heterocyclic rings; and
R$^7$ is hydrogen or contains up to about 50 carbon atoms, generally up to about 30, more generally 20 or fewer, and is selected hydrogen, halide, pseudohalide, alkyl, alkoxy, alkenyl, alkynyl, aryl, aryloxy, heterocycle, aralkyl, aralkoxy, cycloalkyl, cycloalkenyl, cycloalkynyl, OH, ON, C(O)R$^{18}$, CO$_2$R$^{18}$, (CH$_2$)$_r$R$^{18}$, (CH$_2$)$_r$COR$^{18}$ (CH$_2$)$_r$CO(CH$_2$)$_s$R$^{18}$, SH, (CH$_2$)$_r$R$^{18}$, S(O)$_n$R$^{18}$ in which n is 0–2, and s and r are each independently 0 to 6, preferably 1–3, HNOH, NR$^{18}$R$^{19}$, NO$_2$, N$_3$, OR$^{18}$, R$^{19}$NCOR$^{18}$ and CONR$^{19}$R$^{18}$, in which R$^{19}$ is selected from hydrogen, alkyl, alkenyl, alkynyl, aryl, alkylaryl, alkoxy, aryloxy, heterocycle, aralkyl, aralkoxy, cycloalkyl, cycloalkenyl, cycloalkynyl, C(O)R$^{20}$, S(O)$_n$R$^{20}$ in which n is 0–2; and R$^{18}$ and R$^{20}$ are independently selected from hydrogen, alkyl, alkenyl, alkynyl, aryl, alkylaryl, heterocycle, alkoxy, aryloxy, aralkyl, aralkoxy, cycloalkyl, cycloalkenyl or cycloalkynyl; and any of the groups set forth for R$^7$ is unsubstituted or substituted with any substituents set forth for Z, which is hydrogen, halide, pseudohalide, alkyl, alkoxy, alkenyl, alkynyl, aryl, aryloxy, heterocycle, aralkyl, aralkoxy, cycloalkyl, cycloalkenyl, cycloalkynyl, OH, ON, C(O)R$^{21}$, CO$_2$R$^{21}$, SH, S(O)$_n$R$^{21}$ in which n is 0–2, NHOH, NR$^{22}$R$^{21}$, NO$_2$, N$_3$, OR$^{21}$, R$^{22}$NCOR$^{21}$ and CONR$^{22}$R$^{21}$; R$^{22}$ is selected from hydrogen, alkyl, alkenyl, alkynyl, aryl, alkylaryl, heterocycle, aralkyl, alkoxy, aralkoxy, cycloalkyl, cycloalkenyl, cycloalkynyl, C(O)R$^{23}$ and S(O)$_n$R$^{23}$ in which n is 0–2; and R$^{21}$ and R$^{23}$ are independently selected from hydrogen, alkyl, alkenyl, alkynyl, aryl, alkylaryl, heterocycle, aralkyl, aralkoxy, cycloalkyl, cycloalkenyl or cycloalkynyl, and R$^{14}$ is absent.

R$^7$ is preferably C(O)R$^{18}$, CO$_2$R$^{18}$, (CH$_2$)$_r$R$^{18}$, (CH$_2$)$_r$COR$^{18}$ (CH$_2$)$_r$CO(CH$_2$)$_s$R$^{18}$, NR$^{18}$R$^{19}$, OR$^{18}$, R$^{19}$NCOR$^{18}$ or CONR$^{19}$R$^{18}$.

More preferred compounds are those of formula (II) that have formula (III):

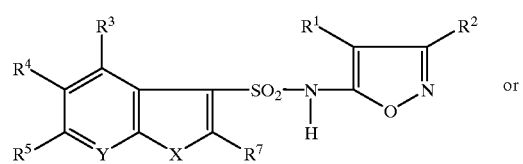

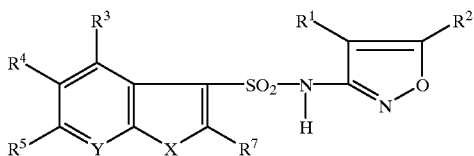

Also of interest of compounds of formula (IV):

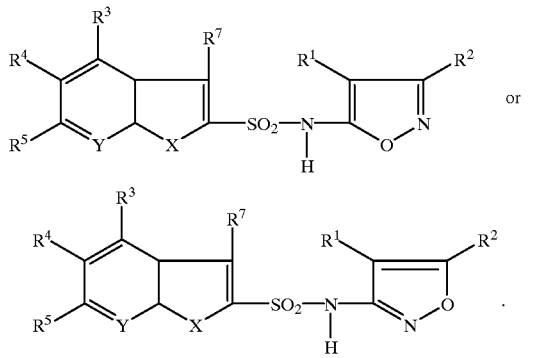

In preferred embodiments of the compounds herein, particularly the compounds of formulae (II) and (III), $R^7$ is $C(O)R^{18}$, $CO_2R^{18}$, $CH_2)_rR^{18}$, $(CH_2)_rC(O)CH_2)_sR^{18}$ $(CH_2)_r$ $R^{18}$, $NR^{18}R^{19}$, $OR^{18}$, $R^{19}$ $NCOR^{18}$ and $CONR^{19}R^{18}$ in which r is 0 to 6, preferably 1–3, When $R^7$, $R^{18}$ or $R^{19}$ is aryl, particularly phenyl, or includes an aryl group, particularly phenyl:

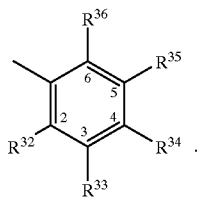

It is unsubstituted or substituted with at positions 2–6 with one or more of $R^{32}$, $R^{33}$, $R^{34}$, $R^{35}$ and $R^{36}$, respectively, which are each independently selected from (i), (ii) or (iii) as follows:

(i) $R^{32}$, $R^{33}$, $R^{34}$, $R^{35}$, and $R^{36}$ are each independently selected from among H, $NHR^{38}$, $CONHR^{38}$, $NO_2$, halide, pseudohalide, alkyl, alkenyl, substituted alkyl or alkenyl, alkynyl, aryl, arylalkyl, heteroaryl, alkoxy, alkylamino, alkylthio, alkoxy, haloalkyl, alkylsulfinyl, alkylsulfonyl, alkoxycarbonyl, alkylcarbonyl, alkenylthio, alkenylamino, alkenyloxy, alkenyl sulfinyl, alkenylsulfonyl, aminocarbonyl, carboxy, carboxyalkyl, carboxyalkenyl, and formyl; or (ii) at least two of $R^{32}$, $R^{33}$, $R^{34}$, $R^{35}$ and $R^{36}$ are substituting adjacent carbons on the ring and together form alkylenedioxy, alkylenethioxyoxy or alkylenedithioxy (i.e. —O—$(CH_2)_n$—O—, —S—$(CH_2)_n$—O—, —S—$(CH_2)_n$—S—, where n is 1 to 4, preferably 1 or 2,) which is unsubstituted or substituted by replacing one or more hydrogens with halide, lower alkyl, lower alkoxy or haloloweralkyl, and the others of $R^{32}$, $R^{33}$, $R^{34}$, $R^{35}$ and $R^{36}$ are selected as in (i); or (iii) at least two of $R^{32}$, $R^{33}$, $R^{34}$, $R^{35}$ and $R^{36}$ are substituting adjacent carbons on the ring and together form alkylenedioxy, alkylenethioxyoxy or alkylenedithioxy (i.e. —O—$(CH_2)_n$—O—, —S—$(CH_2)_n$—O—, —S—$(CH_2)_n$—S—, where n is 1 to 4, preferably 1 or 2,) which is unsubstituted or substituted by replacing one or more hydrogens with halide, lower alkyl, lower alkoxy or haloloweralkyl, and at least two of the others of $R^{33}$, $R^{34}$, $R^{35}$, and $R^{36}$ are substituting adjacent carbons on the ring and together form alkylenedioxy, alkylenethioxyoxy or alkylenedithioxy (i.e. —O—$(CH_2)_n$—O—, —S—$(CH_2)_n$—O—, —S—$(CH_2)_n$—S—, where n is 1 to 4, preferably 1 or 2,) which is unsubstituted or substituted by replacing one or more hydrogens with halide, lower alkyl, lower alkoxy or haloloweralkyl, and the other of $R^{32}$, $R^{33}$, $R^{34}$, $R^{35}$ and $R^{36}$ is selected as in (i); and $R^{38}$ is selected from hydrogen, alkyl, alkenyl, alkynyl, aryl, haloalkyl alkylaryl, heterocycle, arylalkyl, arylalkoxy, alkoxy, aryloxy, cycloalkyl, cycloalkenyl and cycloalkynyl, and is preferably hydrogen, lower alkyl, loweralkoxy and lower haloalkyl.

Preferably, at least one, more preferably two, of $R^{32}$, $R^{33}$, $R^{34}$, $R^{35}$ and $R^{36}$ is H and the others are selected from among (i), (ii) or (iii) as follows:

(i) alkoxy, halo, alkylcarbonyl, formyl, and alkyl, in which the alkyl portions or groups contain from 1 to 3 carbons, provided that at least one of $R^{32}$, $R^{33}$, $R^{34}$, $R^{35}$, and $R^{36}$ is H;

(ii) at least two of $R^{32}$, $R^{33}$, $R^{34}$, $R^{35}$ and $R^{36}$ are substituting adjacent carbons and together form alkylenedioxy and the one of the others of $R^{32}$, $R^{33}$, $R^{34}$, $R^{35}$ and $R^{36}$ are selected as set forth in (i); or (iii) at least two of $R^{32}$, $R^{33}$, $R^{34}$, $R^{35}$ and $R^{36}$ are substituting adjacent carbons and together form alkylenedioxy, and at least two of the others of $R^{32}$, $R^{33}$, $R^{34}$, $R^{35}$ and $R^{36}$ are substituting adjacent carbons and together form alkylenedioxy, and the other of $R^{32}$, $R^{33}$, $R^{34}$, $R^{35}$ and $R^{36}$ is H.

More preferably at least one of $R^{32}$ and $R^{36}$ is not hydrogen.

When $R^7$, $R^{18}$ or $R^{19}$ is pyrimidinyl, it is substituted with one or more substituents selected from (i) or (ii)

(i) H, $NHR^{38}$, $CONHR^{38}$, $NO_2$, halide, pseudohalide, alkyl, alkenyl, substituted alkyl or alkenyl, alkynyl, aryl, arylalkyl, heteroaryl, alkoxy, alkylamino, alkylthio, alkoxy, haloalkyl, alkylsulfinyl, alkylsulfonyl, alkoxycarbonyl, alkylcarbonyl, alkenylthio, alkenylamino, alkenyloxy, alkenyl sulfinyl, alkenylsulfonyl, aminocarbonyl, carboxy, carboxyalkyl, carboxyalkenyl, and formyl; or (ii) at least two substitutents are on adjacent members on the ring and together form alkylenedioxy, alkylenethioxyoxy or alkylenedithioxy (i.e. —O—$(CH_2)_n$—O—, —S—$(CH_2)_n$—O—, —S—$(CH_2)_n$—S—, where n is 1 to 4, preferably 1 or 2,) which is unsubstituted or substituted by replacing one or more hydrogens with halide, lower alkyl, lower alkoxy or haloloweralkyl, and the others substituent(s) are selected as in (i); and $R^{38}$ is selected from hydrogen, alkyl, alkenyl, alkynyl, aryl, haloalkyl alkylaryl, heterocycle, arylalkyl, arylalkoxy, alkoxy, aryloxy, cycloalkyl, cycloalkenyl and cycloalkynyl, and is preferably hydrogen, lower alkyl, loweralkoxy and lower haloalkyl.

In preferred compounds $R^7$ is $(CH_2)_rR^{18}$, and $R^{18}$ is phenyl or pyrimidinyl, preferably phenyl, in which at least two of substituents are on adjacent members of the ring and form alkylenedioxy, one or two remaining substituents are lower alkyl or lower alkoxy, preferably methyl or methoxy, more preferably methyl, and the any others are hydrogen.

In preferred compounds of all of the embodiments herein, Y is preferably N, and X is preferably S or O, more preferably S.

Among the preferred compounds are those set forth in Table 1:

TABLE 1*

| COMPOUND | $ET_A$ $(\mu M)^\dagger$ | $ET_B$ $(\mu M)^\dagger$ |
|---|---|---|
| N-(4-chloro-3-methyl-5-isoxazolyl)-2-ethylthieno-[2,3-b]pyridine-3-sulfonamide | .068 | 39 |
| N-(4-chloro-5-methyl-3-isoxazolyl)-2-ethylthieno[2,3-b]pyridine-3-sulfonamide | .045 | 30 |
| N-(4-chloro-3-methyl-5-isoxazolyl)thieno[2,3-b]-pyridine-3-sulfonamide | 1.8 | >100 |
| N-(4-chloro-3-methyl-5-isoxazolyl)-2-[(3,4-methylenedioxy)benzoyl]thieno[2,3-b]pyridine-3-sulfonamide | 0.96 | 31 |
| N-(4-chloro-3-methyl-5-isoxazolyl)-2-[(3,4-methylenedioxy)benzyl]thieno[2,3-b]pyridine-3-sulfonamide | 0.0056 | 2.8 |
| N-(4-chloro-3-methyl-5-isoxazolyl)-2-[(4,5-methylenedioxy)-2-methylbenzyl]thieno[2,3-b]pyridine-3-sulfonamide | 0.0015 | 1.6 |
| N-(4-chloro-3-methyl-5-isoxazolyl)-2-[(2,4-dimethyl)-benzyl)thieno[2,3-b]pyridine-3-sulfonamide | 0.0045 | 1.5 |
| N-(4-chloro-5-methyl-3-isoxazolyl)-2-[(4,5-methylenedioxy)-2-methylbenzyl)thieno[2,3-b]pyridine-3-sulfonamide | 0.0010 | 0.5 |
| N-(4-chloro-3-methyl-5-isoxazolyl)-2-{(4,5-methylenedioxy)-2-[(hydroxyethyl)-benzyl]}thieno[2,3-b]pyridine-3-sulfonamide | 0.0015 | 3.6 |
| N-(4-chloro-3-methyl-5-isoxazolyl)-2-[1-naphthalenemethyl)thieno[2,3-b]pyridine-3-sulfonamide | 0.034 | 0.56 |
| N-(4-chloro-3-methyl-5-isoxazolyl)-2-[(2,6-dimethoxy)benzyl]thieno[2,3-b]pyridine-3-sulfonamide | 0.65 | 10.1 |
| N-(4-chloro-3-methyl-5-isoxazolyl)-2-[3-(3,4 methylenedioxyphenyl)propionyl]thieno[2,3-b]pyridine-3-sulfonamide | 0.045 | 6.6 |

$^\dagger$assay performed with incubation at 24° C. As described in the Examples, incubation at this higher temperature reduces the activity by a factor of 2- to about 10-compared to the activity at 4° C.
*results are generally the average of 2 to 3 experiments
— data not available or measured as % inhibition @ 100 $\mu M$
% = % inhibition @ 100 $\mu M$ B. Preparation of the Compounds The preparation of the above compounds are described in detail in the examples. Any such compound or similar compound may be synthesized according to a method discussed in general below and set forth in the Examples by selecting appropriate starting materials as exemplified.

In general, most of the syntheses involve the condensation of a sulfonyl chloride with an aminoisoxazole in dry pyridine or in tetrahydrofuran (THF) and sodium hydride. The sulfonyl chlorides and aminoisoxazoles either can be obtained commercially or synthesized according to methods described in the Examples or using other methods available to those of skill in this art (see, e.g., U.S. Pat. Nos. 4,659,369, 4,861,366 and 4,753,672).

The N-(alkylisoxazolyl)sulfonamides can be prepared by condensing an aminoisoxazole with a sulfonyl chloride in dry pyridine with or without the catalyst 4-(dimethylamino) pyridine. The N-(3,4-dimethyl-5-isoxazolyl)sulfonamides and N-(4,5-dimethyl-3-isoxazolyl)sulfonamides can be prepared from the corresponding aminodimethylisoxazole, such as 5-amino-3,4-dimethylisoxazole. For example, N-(3, 4-dimethyl-5-isoxazolyl)-2-(carbomethoxy)thiophene-3-sulfonamide was prepared from 2-methoxycarbonylthiophene-3-sulfonyl chloride and 5-amino-3,4-dimethylisoxazole in dry pyridine.

The N-(4-haloisoxazolyl)sulfonamides can be prepared by condensation of amino-4-haloisoxazole with a sulfonyl chloride in THF with sodium hydride as a base. For example, N-(4-bromo-3-methyl-5-isoxazolyl)thiophene-2-sulfonamide was prepared from 5-amino-4-bromo-3-methylisoxazole and thiophene-2-sulfonyl chloride in THF and sodium hydride. N-(4-bromo-3-methyl-5-isoxazolyl)-5-(3-isoxazolyl)thiophene-2-sulfonamide was prepared from 5-amino-4-bromo-3-methylisoxazole and 5-(3-isoxazolyl)thiophene-2-sulphonyl chloride.

Alternatively, compounds, such as those in which $Ar^2$ is thienyl, furyl and pyrrolyl herein, may be prepared by reacting an appropriate sulfonyl chloride with a 5-aminoisoxazole substituted at the 3 and 4 positions, such as 5-amino-4-bromo-3-methylisoxazole, in tetrahydrofuran (THF) solution containing a base, such as sodium hydride. Following the reaction, the THF is removed under reduced pressure, the residue dissolved in water, acidified and extracted with methylene chloride. The organic layer is washed and then dried over anhydrous magnesium sulfate, the solvents are evaporated and the residue is purified by recrystallization using hexanes/ethylacetate to yield pure product.

These sulfonamides also can be prepared from the corresponding sulfonyl chloride and the aminoisoxazole in pyridine with or without a catalytic amount of 4-dimethylaminopyridine (DMAP). In some cases, the bis-sulfonyl compound is obtained as the major or exclusive product. The bis-sulfonated products can be readily hydrolyzed to the sulfonamide using aqueous sodium hydroxide and a suitable co-solvent, such as methanol or tetrahydrofuran, generally at room temperature.

To prepare the thieno-pyridine sulfonamides, a thieno[2,3-b]pyridine is reacted with chlorosulfonic acid to produce a thieno[2,3-b]pyridine-3-sulfonamide, which is then reacted with a 4-chloro-5-methyl-3-aminoisoxazole to produce the desired thieno-pyridine. Preparation of exemplary thieno-pyridines are set forth in the EXAMPLES.

Prodrugs and other derivatives of the compounds suitable for administration to humans may also be designed and prepared by methods known to those of skill in the art (see, e.g., Nogrady (1985) *Medicinal Chemistry A Biochemical Approach,* Oxford University Press, New York, pages 388–392).

Compounds described herein have been synthesized and tested for activity in in vitro assays and, in some cases, in in vivo animal models. Nuclear magnetic resonance spectroscopic (NMR), mass spectrometric, infrared spectroscopic and high performance liquid chromatographic analyses indicated that the synthesized compounds have structures consistent with those expected for such compounds and are generally at least about 98% pure. All of the compounds exemplified or described herein exhibited activity as endothelin antagonists.

C. Evaluation of the Bioactivity of the Compounds

Standard physiological, pharmacological and biochemical procedures are available for testing the compounds to identify those that possess any biological activities of an endothelin peptide or the ability to interfere with or inhibit endothelin peptides. Compounds that exhibit in vitro activities, such as the ability to bind to endothelin receptors or to compete with one or more of the endothelin peptides for binding to endothelin receptors can be used in the methods for isolation of endothelin receptors and the methods for distinguishing the specificities of endothelin receptors, and are candidates for use in the methods of treating endothelin-mediated disorders.

Thus, other preferred compounds of formulas I and II, in addition to those specifically identified herein, that are endothelin antagonists or agonists may be identified using such screening assays.

1. Identifying Compounds that Modulate the Activity of an Endothelin Peptide

The compounds are tested for the ability to modulate the activity of endothelin-1. Numerous assays are known to those of skill in the art for evaluating the ability of compounds to modulate the activity of endothelin (see, e.g., U.S. Pat. No. 5,114,918 to Ishikawa et al.; EP A1 0 436 189 to BANYU PHARMACEUTICAL CO., LTD. (Oct. 7, 1991); Borges et al. (1989) *Eur. J. Pharm.* 165: 223–230; Filep et al. (1991) *Biochem. Biophys. Res. Commun.* 177: 171–176). In vitro studies may be corroborated with in vivo studies (see, e.g., U.S. Pat. No. 5,114,918 to Ishikawa et al.; EP A1 0 436 189 to BANYU PHARMACEUTICAL CO., LTD. (Oct. 7, 1991)) and pharmaceutical activity thereby evaluated. Such assays are described in the Examples herein and include the ability to compete for binding to $ET_A$ and $ET_B$ receptors present on membranes isolated from cell lines that have been genetically engineered to express either $ET_A$ or $ET_B$ receptors on their cell surfaces.

The properties of a potential antagonist may be assessed as a function of its ability to inhibit an endothelin induced activity in vitro using a particular tissue, such as rat portal vein and aorta as well as rat uterus, trachea and vas deferens (see e.g., Borges, R., Von Grafenstein, H. and Knight, D. E., "Tissue selectivity of endothelin," *Eur. J. Pharmacol* 165:223–230, (1989)). The ability to act as an endothelin antagonist in vivo can be tested in hypertensive rats, ddy mice or other recognized animal models (see, Kaltenbronn et al. (1990) *J. Med. Chem.* 33:838–845, see, also, U.S. Pat. No. 5,114,918 to Ishikawa et al.; and EP A1 0 436 189 to BANYU PHARMACEUTICAL CO., LTD (Oct. 7, 1991); see, also Bolger et al. (1983) *J. Pharmacol. Exp. Ther.* 225291–309). Using the results of such animal studies, pharmaceutical effectiveness may be evaluated and pharmaceutically effective dosages determined. A potential agonist may also be evaluated using In vitro and in vivo assays known to those of skill in the art.

Endothelin activity can be identified by the ability of a test compound to stimulate constriction of isolated rat thoracic aorta (Borges et al. (1989) "Tissue selectivity of endothelin" *Eur. J. Pharmacol.* 165: 223–230). To perform the assay, the endothelium is abraded and ring segments mounted under tension in a tissue bath and treated with endothelin in the presence of the test compound. Changes in endothelin induced tension are recorded. Dose response curves may be generated and used to provide information regarding the relative inhibitory potency of the test compound. Other tissues, including heart, skeletal muscle, kidney, uterus, trachea and vas deferens, may be used for evaluating the effects of a particular test compound on tissue contraction.

Endothelin isotype specific antagonists may be identified by the ability of a test compound to interfere with endothelin binding to different tissues or cells expressing different endothelin-receptor subtypes, or to interfere with the biological effects of endothelin or an endothelin isotype (Takayanagi et al. (1991) *Reg. Pep.* 32: 23–37, Panek et al. (1992) *Biochem. Biophys. Res. Commun.* 183: 566–571). For example, $ET_B$ receptors are expressed in vascular endothelial cells, possibly mediating the release of prostacyclin and endothelium-derived relaxing factor (De Nucci et al. (1988) *Proc. Natl. Acad. Sci. USA* 85:9797). $ET_A$ receptors are not detected in cultured endothelial cells, which express $ET_B$, receptors.

The binding of compounds or inhibition of binding of endothelin to $ET_B$ receptors can be assessed by measuring the inhibition of endothelin-1-mediated release of prostacyclin, as measured by its major stable metabolite, 6-keto $PGF_{1\alpha}$, from cultured bovine aortic endothelial cells (see, eg., Filep et al. (1991) *Biochem, and Biophys Res. Commun.* 177: 171–176). Thus, the relative affinity of the compounds for different endothelin receptors may be evaluated by determining the inhibitory dose response curves using tissues that differ in receptor subtype.

Using such assays, the relative affinities of the compounds for $ET_A$ receptors and $ET_B$ receptors have been and can be assessed. Those that possess the desired properties, such as specific inhibition of binding of endothelin-1, are selected. The selected compounds that exhibit desirable activities may be therapeutically useful and are tested for such uses using the above-described assays from which in vivo effectiveness may be evaluated (see, e.g., U.S. Pat. Nos. 5,248,807; 5,240,910; 5,198,548; 5,187,195; 5,082,838; 5,230,999; published Canadian Application Nos. 2,067,288 and 2071193; published Great Britain Application No. 2,259, 450; Published International PCT Application No. WO 93/08799; Benigi et al. (1993) *Kidney International* 44:440–444; and Nirei et al. (1993) *Life Sciences* 52:1869–1874). Compounds that exhibit in vitro activities that correlate with in vivo effectiveness will then be formulated in suitable pharmaceutical compositions and used as therapeutics.

The compounds also may be used in methods for identifying and isolating endothelin-specific receptors and aiding in the design of compounds that are more potent endothelin antagonists or agonists or that are more specific for a particular endothelin receptor.

2. Isolation of Endothelin Receptors

A method for identifying endothelin receptors is provided. In practicing this method, one or more of the compounds is linked to a support and used in methods of affinity purification of receptors. By selecting compounds with particular specificities, distinct subclasses of ET receptors may be identified.

One or more of the compounds may be linked to an appropriate resin, such as Affi-gel, covalently or by other linkage, by methods known to those of skill in the art for linking endothelin to such resins (see, Schvartz et al. (1990) *Endocrinology* 126: 3218–3222). The linked compounds can be those that are specific for $ET_A$ or $ET_B$ receptors or other subclass of receptors.

The resin is pre-equilibrated with a suitable buffer generally at a physiological pH (7 to 8). A composition containing solubilized receptors from a selected tissue are mixed with the resin to which the compound is linked and the receptors are selectively eluted. The receptors can be identified by testing them for binding to an endothelin isopeptide or analog or by other methods by which proteins are identified and characterized. Preparation of the receptors, the resin and the elution method may be performed by modification of standard protocols known to those of skill in the art (see, e.g. Schvartz et al. (1990) *Endocrinology* 126: 3218–3222).

Other methods for distinguishing receptor type based on differential affinity to any of the compounds herein are provided. Any of the assays described herein for measuring the affinity of selected compounds for endothelin receptors may also be used to distinguish receptor subtypes based on affinity for particular compounds provided herein. In particular, an unknown receptor may be identified as an $ET_A$ or $ET_B$ receptor by measuring the binding affinity of the unknown receptor for a compound provided herein that has a known affinity for one receptor over the other. Such preferential interaction is useful for determining the particular disease that may be treated with a compound prepared as described herein. For example, compounds with high affinity for $ET_A$ receptors and little or no affinity for $ET_B$ receptors are candidates for use as hypertensive agents; whereas, compounds that preferentially interact with $ET_B$ receptors are candidates for use as anti-asthma agents.

D. Formulation and Administration of the Compositions

Effective concentrations of one or more of the sulfonamide compounds of formula I or II or any formula or compound provided herein or pharmaceutically acceptable salts, esters or other derivatives thereof are mixed with a suitable pharmaceutical carrier or vehicle. In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as tween, or dissolution in aqueous sodium bicarbonate. Derivatives of the compounds, such as salts of the compounds or prodrugs of the compounds may also be used in formulating effective pharmaceutical compositions.

The concentrations or the compounds are effective for delivery of an amount, upon administration, that ameliorates the symptoms of the endothelin-mediated disease. Typically, the compositions are formulated for single dosage administration.

Upon mixing or addition of the sulfonamide compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

Pharmaceutical carriers or vehicles suitable for administration of the compounds provided herein include any such carriers known to those skilled in the art to be suitable for the particular mode of administration. In addition, the compounds may be formulated as the sole pharmaceutically active ingredient in the composition or may be combined with other active ingredients.

The active compounds can be administered by any appropriate route, for example, orally, parenterally, intravenously, intradermally, subcutaneously, or topically, in liquid, semi-liquid or solid form and are formulated in a manner suitable for each route of administration. Preferred modes of administration include oral and parenteral modes of administration.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in known in vitro and in vivo systems (see, e.g., U.S. Pat. No. 5,114,918 to Ishikawa et al.; EP A1 0 436 189 to BANYU PHARMACEUTICAL CO., LTD (Oct. 7, 1991); Borges et al. (1989) Eur. J. Pharm. 165: 223–230;: Filep et al. (1991) Biochem. Biophys. Res. Commun. 177: 171–176) and then extrapolated therefrom for dosages for humans.

The concentration of active compound in the drug composition will depend on absorption, inactivation and excretion rates of the active compound, the dosage schedule, and amount administered as well as other factors known to those of skill in the art. For example, the amount that is delivered is sufficient to treat the symptoms of hypertension. The effective amounts for treating endothelin-mediated disorders are expected to be higher than the amount of the sulfonamide compound that would be administered for treating bacterial infections.

Typically a therapeutically effective dosage should produce a serum concentration of active ingredient of from about 0.1 $\mu$g/ml to about 50–100 $\mu$g/ml. The pharmaceutical compositions typically should provide a dosage of from about 0.01 mg to about 2000 mg of compound per kilogram of body weight per day. The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

If oral administration is desired, the compound should be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

Oral compositions will generally include an inert diluent or an edible carrier and may be compressed into tablets or enclosed in gelatin capsules. For the purpose of oral therapeutic administration, the active compound or compounds can be incorporated with excipients and used in the form of tablets, capsules or troches. Pharmaceutically compatible binding agents and adjuvant materials can be included as part of the composition.

The tablets, pills, capsules, troches and the like can contain any of the following ingredients, or compounds of a similar nature: a binder, such as microcrystalline cellulose, gum tragacanth and gelatin; an excipient such as starch and lactose, a disintegrating agent such as, but not limited to, alginic acid and corn starch; a lubricant such as, but not limited to, magnesium stearate; a glidant, such as, but not limited to, colloidal silicon dioxide; a sweetening agent such as sucrose or saccharin; and a flavoring agent such as peppermint, methyl salicylate, and fruit flavoring.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. For example, if the compound is used for treating asthma or hypertension, it may be used with other bronchodilators and antihypertensive agents, respectively.

Solutions or suspensions used for parenteral, intradermal, subcutaneous, or topical application can include any of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, disposable syringes or multiple dose vials made of glass, plastic or other suitable material.

If administered intravenously, suitable carriers include physiological saline or phosphate buffered saline (PBS), and solutions containing thickening and solubilizing agents, such as glucose, polyethylene glycol, and polypropylene glycol and mixtures thereof. Liposomal suspensions, including tissue-targeted liposomes, may also be suitable as pharmaceutically acceptable carriers. These may be prepared according to methods known to those skilled in the art. For example, liposome formulations may be prepared as described in U.S. Pat. No. 4,522,811.

The active compounds may be prepared with carriers that protect the compound against rapid elimination from the body, such as time release formulations or coatings. Such carriers include controlled release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of such formulations are known to those skilled in the art.

The compounds may be formulated for local or topical application, such as for topical application to the skin and mucous membranes, such as in the eye, in the form of gels, creams, and lotions and for application to the eye or for intracisternal or intraspinal application. Such solutions, particularly those intended for ophthalmic use, may be formulated as 0.01%–10% isotonic solutions, pH about 5–7, with appropriate salts. The compounds may be formulated as aerosols for topical application, such as by inhalation (see, e.g., U.S. Pat. Nos. 4,044,126, 4,414,209, and 4,364,923, which describe aerosols for delivery of a steroid useful for treatment inflammatory diseases, particularly asthma).

Finally, the compounds may be packaged as articles of manufacture containing packaging material, a compound provided herein, which is effective for antagonizing the effects of endothelin, ameliorating the symptoms of an endothelin-mediated disorder, or inhibiting binding of an endothelin peptide to an ET receptor with an $IC_{50}$ of less than about 10 μM, within the packaging material, and a label that indicates that the compound or salt thereof is used for antagonizing the effects of endothelin, treating endothelin-mediated disorders or inhibiting the binding of an endothelin peptide to an ET receptor.

The following examples are included for illustrative purposes only and are not intended to limit the scope of the invention.

EXAMPLE 1

N-(4-chloro-3-methyl-5-isoxazolyl)-2-ethylthieno[2,3-b]pyridine-3-sulfonamide

A. 2-Ethylthieno[2,3-b]pyridine

To a solution of thieno[2,3-b]pyridine (0.35 g, 2.6 mmoles) prepared according to well known methods [see, Klemm, et al. (1969) *J. Org. Chem.*, 34:347–354; see, also U.S. Pat. Nos. 5,026,700, 4,577,014, 4,406,898, 4,375,544, 4,311,845, and 4,161,599] in THF (10 ml) at −78° C. was added t-BuLi (1.7 M, 2.0 ml, 3.4 mmoles). The reaction solution was slowly warmed to −30° C. over a 45 minute period followed by the addition of bromoethane (0.25 ml, 3.4 mmoles). The solution was stirred 2 hours at ambient temperature then diluted with EtOAc (50 ml) and washed with $H_2O$ (75 ml). The organic phase was dried ($MgSO_4$), filtered and concentrated to collect 0.41 g (97%) of the title compound as an orange-brown oil.

B. 2-ethylthieno[2,3-b]pyridine-3-sulfonyl chloride

To a solution of 2-ethylthieno[2,3-b]pyridine (0.43 g, 2.6 mmoles) in $CH_2Cl_2$ (10 ml) at −78° C. was added chlorosulfonic acid (0.9 ml, 13 mmoles). The reaction was warmed to ambient temperature over a 1 hr. period, then stirred an additional 20 hrs., followed by the addition of phosphorus oxychloride (1.7 ml, 18 mmoles) and phosphorus pentachloride (0.82 g, 4.0 mmoles). One hour later the reaction mixture was added to ice (100 ml) and extracted with EtOAc (75 ml), then washed with sat. $NaHCO_3$ (200 ml). The organic phase was dried ($MgSO_4$), filtered and concentrated to collect a brown oil. Flash chromatography (10% EtOAc/hexanes) provided 0.39 g (56%) of the title compound as a light yellow oil.

C. N-(4-chloro-3-methyl-5-isoxazolyl)-2-ethylthieno[2,3-b]-pyridine-3-sulfonamide To a mixture of NaH (38 mg, 1.6 mmoles) in THF (5 ml) at ambient temperature was added 4-chloro-3-methyl-5-amino isoxazole (84 mg, 0.63 mmoles). The mixture was stirred 1 hr. at ambient temperature then cooled to 0° C. followed by the addition of 2-ethylthieno[2,3-b]pyridine-3-sulfonyl chloride (0.19 g, 0.73 mmoles) via cannula in THF (2 ml). The cooling bath was removed and the brown mixture was stirred 1 hr. at ambient temperature and then diluted with 3% NaOH (50 ml) and washed with $CHCl_3$ (2×75 ml). The aqueous layer was acidified to pH 4 using concentrated HCl, upon which a precipitate formed. The aqueous phase was extracted with EtOAc (50 ml), and the organic layer was dried ($MgSO_4$), filtered and concentrated to collect 0.23 g of a yellow oil. Recrystallization from EtOAc/hexanes provided 0.18 g (79%) of the title compound as a light yellow solid, m.p. 152–154° C.

EXAMPLE 2

N-(4-chloro-5-methyl-3-isoxazolyl)-2-ethylthieno[2,3-b]pyridine-3-sulfonamide

N-(4-chloro-5-methyl-3-isoxazolyl)-2-ethylthieno[2,3-b]pyridine-3-sulfonamide was prepared according to Example 1 (C), using NaH (44 mg, 1.9 mmoles), THF (5 ml), 4-chloro-5-methyl-3-aminoisoxazole (82 mg, 0.62 mmoles) and 2-ethylthieno[2,3-b]pyridine-3-sulfonyl chloride (0.19 g, 0.71 mmoles). Flash chromatography (50% EtOAc/hexanes) followed by recrystallization from EtOAc/hexanes provided 78 mg (35%) of the title compound as a light yellow solid, m.p. 172–174° C.

EXAMPLE 3

N-(4-chloro-3-methyl-5-isoxazolyl)thieno[2,3-b]pyridine-3-sulfonamide

A. Thieno[2,3-b]pyridine-3-sulfonyl chloride

A solution of thieno[2,3-b]pyridine (0.70 g, 5.2 mmoles), prepared as described in Example 1 (A), in chlorosulfonic acid, (7 ml) was heated to 100° C. for 15 minutes, then cooled to ambient temperature and added to ice (100 ml). The pH of the aqueous phase as adjusted to 8 with sat.

NaHCO$_3$, then extracted with CHCl$_3$ (2×125 ml). The organic phase was dried (MgSO$_4$), filtered and concentrated to collect 0.95 g (78%) of the title compound as a tan solid.

B. N-(4-chloro-3-methyl-5-isoxazolyl)thieno[2,3-b]pyridine-3-sulfonamide

N-(4-chloro-3-methyl-5-isoxazolyl)thieno[2,3-b]pyridine-3-sulfonamide was prepared by the method of Example 1(C) using NaH (0.16 g, 6.8 mmoles), THF (10 ml), 4-chloro-3-methyl-5-aminoisoxazole (0.36 g, 2.7 mmoles) and thieno[2,3-b]pyridine-3-sulfonyl chloride (0.70 g, 3.0 mmoles) to provide 0.86 g (96%) of the title compound as a tan solid. Recrystallization of 56 mg from EtOAc/hexanes provided 43 mg of a light tan solid, m.p. 176–177° C.

EXAMPLE 4

N-(4-chloro-3-methyl-5-isoxazolyl)-2-[3,4-(methylenedioxy)benzoyl]-thieno [2,3-b]pyridine-3-sulfonamide A. N-(4-chloro-3-methyl-5-isoxazolyl)-N-(methoxyethoxymethyl)-thieno [2,3-b]pyridine-3-sulfonamide To a solution of N-(4-chloro-3-methyl-5-isoxazolyl)thieno[2,3-b]-pyridine -3-sulfonamide (0.76 g, 2.3 mmoles) (see Example 3), DIEA (0.6 ml, 35 mmoles) and EtOAc (100 ml) was added MEM-Cl (0.3 ml, 2.5 mmoles). The orange-brown solution was stirred 3 hours at ambient temperature, then washed with saturated NaHCO$_3$ (200 ml). The organic layer was dried (MgSO$_4$), filtered and concentrated to collect 0.92 g (95%) of the title compound as a brown solid.

B. N-(4-chloro-3-methyl-5-isoxazolyl)-N-(methoxyethoxymethyl)-2-[α-hydroxy-3,4-(methylenedioxy)benzyl]thieno[2,3-b]-pyridine-3-sulfonamide To a solution of N-(4-chloro-3-methyl-5-isoxazolyl)-N-(methoxyethoxymethyl)thieno [2,3-b]pyridine-3-sulfonamide (0.25 g, 0.61 mmoles) in THF (10 ml) at −78° C. was added t-BuLi (1.7 M, 0.46 ml, 0.79 mmoles). Thirty minutes later piperonal (0.14 g, 0.91 mmoles) in THF (2 ml) was added via cannula, as a solution. The cooling bath was removed and the reaction was stirred 1 hr. at ambient temperature and then diluted with EtOAc (50 ml) and washed with H$_2$O (2×75 ml). The organic layer was dried (MgSO$_4$), filtered and concentrated. Flash chromatography (40% EtOAc/hexanes) provided 0.15 g (44%) of the title compound as a white foamy solid.

C. N-(4-chloro-3-methyl-5-isoxazolyl)-N-(methoxyethoxymethyl)-2 -[3,4-(methylenedioxy)benzoyl]thieno [2,3-b]pyridine-3-sulfonamide To a solution of N-(4-chloro-3-methyl-5-isoxazolyl)-N-(methoxyethoxymethyl)-2 -[μ-hydroxy-3,4-(methylenedioxy)benzyl]thieno-[2,3-b]pyridine-3-sulfonamide (0.15 g, 0.27 mmoles) in CH$_2$Cl$_2$ (3 ml) was added manganese dioxide (72 mg, 0.83 mmoles). The black mixture was stirred 24 hours at ambient temperature then filtered and concentrated to collect 0.15 g (96%) of the title compound as a light yellow solid.

D. N-(4-chloro-3-methyl-5-isoxazolyl)-2-[3,4-(methylenedioxy)-benzoyl]thieno[2,3-b]pyridine-3-sulfonamide A solution of N-(4-chloro-3-methyl-5-isoxazolyl)-N-(methoxyethoxy-methyl)-2 -[3,4-(methylenedioxy)benzoyl]thieno[2,3-b]pyridine-3-sulfonamide (0.15 g, 0.26 mmoles) in methanol (5 ml) and 4N HCl (2 ml) was heated to reflux for 3 hours then cooled to ambient temperature and concentrated. The residue was diluted with EtOAc (50 ml) and washed with saturated NaCl (2×50 ml). The organic layer was dried (MgSO$_4$), filtered and concentrated to collect 0.10 g (81 %) of the title compound as a foamy yellow solid, m.p. 75–90° C.

EXAMPLE 5

N-(4-chloro-3-methyl-5-isoxazolyl)-2-[3,4-(methylenedioxy)benzyl]thieno [2,3-b]pyridine-3-sulfonamide A. N-(4-chloro-3-methyl-5-isoxazolyl)-N-(methoxyethoxymethyl)-2 -[3,4-(methylenedioxy)benzyl]thieno[2,3-b]pyridine-3-sulfonamide To a solution of N-(4-chloro-3-methyl-5-isoxazolyl)-N-(methoxyethoxymethyl)-2 -(α-hydroxy-3,4-(methylenedioxy) benzyl]-thieno [2,3-b]pyridine-3-sulfonamide (0.10 g, 0.18 mmoles)[see Example 4(B)] and triethylsilane (0.29 ml, 1.8 mmoles) in CH$_2$Cl$_2$ (2 ml) was added boron trifluoride etherate (0.10 ml, 0.81 mmoles). The orange-brown solution was stirred 2 hours at ambient temperature then diluted with EtOAc (50 ml) and washed with H$_2$O (75 ml). The organic layer was dried (MgSO$_4$), filtered and concentrated to collect an orange oil. Flash chromatography (40% EtOAc/hexanes) provided 66 mg (66%) of the title compound as a yellow oil.

B. N-(4-chloro-3-methyl-5-isoxazolyl)-2-[3,4-(methylenedioxy)-benzyl]thieno[2,3-b]pyridine-3-sulfonamide The title compound was prepared by the method of Example 4(D) using N-(4-chloro-3-methyl-5-isoxazolyl)-N-(methoxyethoxymethyl)-2-[3,4-(methylenedioxy)benzyl] thieno[2,3-b]pyridine-3-sulfonamide (0.14 g, 0.26 mmoles), methanol (6 ml) and 4N HCl (2 ml). Recrystallization from chloroform/hexanes provided 91 mg (76%) of the title compound as a tan crystalline solid, m.p. 163.5–165° C.

EXAMPLE 6

N-(4-chloro-3-methyl-5-isoxazolyl)-2-[2-methyl-4,5-(methylene-dioxy)benzyl]thieno [2,3-b]pyridine-3-sulfonamide A. 2-Methyl-4,5-(methylenedioxy)benzaldehyde To DMF (6.5 ml, 83 mmoles) at 0° C. was added phosphorus oxychloride (3.9 ml, 42 mmoles). The solution was stirred 15 minutes at 0° C. followed by the addition of 3,4-(methylenedioxy)toluene (1.0 ml, 8.3 mmoles). The solution was heated to 110° C. upon which it became dark brown. 1.5 hours later the thick dark brown mixture was cooled to ambient temperature then added to ice (100 ml), and extracted with ether (100 ml). The organic layer was dried (MgSO$_4$), filtered and concentrated. Flash chromatography (5% EtOAc/hexanes) provided 0.15 g (11%) of the title compound as a colorless oil.

B. N-(4-chloro-3-methyl-5-isoxazolyl)-N-(methoxyethoxymethyl)-2 -[α-hydroxy-2-methyl-4,5-(methylenedioxy)-benzyl]thieno[2,3-b]pyridine-3-sulfonamide The title compound was prepared by the method of Example 4(B) using N-(4-chloro-3-methyl-5-isoxazolyl)-N-(methoxyethoxy-methyl)thieno [2,3-b]pyridine-3-sulfonamide (0.31 g, 0.75 mmoles)[Example 4(A)], THF (4 ml), t-BuLi (1.7 M, 0.53 ml, 0.90 mmoles) and 2-methyl-4,5-(methylenedioxy)benzaldehyde (0.15 g, 0.90 mmoles). Flash chromatography (40% EtOAc/hexanes) provided 0.16 g (38%) of the title compound.

C. N-(4-chloro-3-methyl-5-isoxazolyl)-N-(methoxyethoxymethyl)-2-[2-methyl-4,5-(methylenedioxy)benzyl]thieno[2,3-b]pyridine-3-sulfonamide The title compound was prepared by the method of Example 5(A), using N-(4-chloro-3-methyl-5-isoxazolyl)-N-(methoxyethoxymethyl)-2-[α-hydroxy-2-methyl-4,5-(methylenedioxy)benzyl]thieno[2,3-b]pyridine-3-sulfonamide (0.16 g, 0.28 mmoles), $CH_2Cl_2$ (3 ml), triethylsilane (0.45 ml, 2.8 mmoles) and boron trifluoride etherate (0.17 ml, 1.4 mmoles). Flash chromatography (40% EtOAc/hexanes) provided 0.13 g (82%) of the title compound.

D. N-(4-chloro-3-methyl-5-isoxazolyl)-2-[2-methyl-4,5-(methylenedioxy)benzyl]thieno[2,3-b]pyridine-3-sulfonamide The title compound was prepared by the method of Example 4(D) using N-(4-chloro-3-methyl-5-isoxazolyl)-N-(methoxyethoxymethyl)-2-[2-methyl-4,5-(methylenedioxy)benzyl]thieno[2,3-b]pyridine-3-sulfonamide (0.13 g, 0.23 mmoles), methanol (6 ml) and 4N HCl (2 ml). Recrystallization from chloroform/hexanes provided 70 mg (63%) of the title compound as a white crystalline solid, m.p. 182–184° C.

EXAMPLE 7

N-(4-chloro-3-methyl-5-isoxazolyl)-2-(2,4-dimethylbenzyl)thieno[2,3-b]pyridine-3-sulfonamide A. N-(4-chloro-3-methyl-5-isoxazolyl)-N-(methoxyethoxymethyl)-2-[α-hydroxy-2,4-dimethylbenzyl]thieno[2,3-b]pyridine-3-sulfonamide The title compound was prepared by the method of Example 4(B) using N-(4-chloro-3-methyl-5-isoxazolyl)-N-(methoxyethoxy-methyl)thieno[2,3-b]pyridine-3-sulfonamide (0.18 g, 0.42 mmoles)[Example 4(A)], t-BuLi (1.7 M, 0.32 ml, 0.55 mmoles), THF (5 ml) and 2,4-dimethylbenzaldehyde (0.12 ml, 0.84 mmoles). Flash chromatography (40% EtOAc/hexanes) provided 0.17 g (73%) of the title compound.

B. N-(4-chloro-3-methyl-5-isoxazolyl)-N-(methoxyethoxymethyl)-2-(2,4-dimethylbenzyl)thieno[2,3-b]pyridine-3-sulfonamide The title compound was prepared by the method of Example 5(A) using N-(4-chloro-3-methyl-5-isoxazolyl)-N-(methoxyethoxymethyl)-2-[α-hydroxy-2,4-dimethylbenzyl]thieno[2,3-b]pyridine-3-sulfonamide (0.1 7 g, 0.31 mmoles), $CH_2Cl_2$ (5 ml), triethylsilane (0.5 ml, 3.1 mmoles) and boron trifluoride etherate (0.2 ml, 1.5 mmoles). Flash chromatography (40% EtOAc/hexanes) provided 87 mg (53%) of the title compound.

C. N-(4-chloro-3-methyl-5-isoxazolyl)-2-(2,4-dimethylbenzyl)-thieno[2,3-b]pyridine-3-sulfonamide The title compound was prepared by the method of Example 4(D) using N-(4-chloro-3-methyl-5-isoxazolyl)-N-(methoxyethoxymethyl)-2-(2,4-dimethylbenzyl)thieno[2,3-b]pyridine-3-sulfonamide (87 mg, 0.16 mmoles), methanol (3 ml) and 4N HCl (1 ml). Recrystallization from chloroform/hexane provided 52 mg (72%) of the title compound as a white crystalline solid, m.p. 123–125° C.

EXAMPLE 8

N-(4-chloro-5-methyl-3-isoxazolyl)-2-[2-methyl-4,5-(methylenedioxy)-benzyl]thieno[2,3-b]pyridine-3-sulfonamide A. N-(4-chloro-5-methyl-3-isoxazolyl)thieno[2,3-b]pyridine-3-sulfonamide The title compound was prepared by the method of Example 1(C) using NaH (0.12 g, 4.9 mmoles), THF (6 ml), 4-chloro-5-methyl-3-aminoisoxazole (0.26 g, 2.0 mmoles) and thieno[2,3-b]pyridine-3-sulfonyl chloride (0.50 g, 2.1 mmoles), giving 0.30 g (47%) of the title compound as an orange-brown oil.

B. N-(4-chloro-5-methyl-3-isoxazolyl)-N-(methoxyethoxymethyl)-thieno[2,3-b]pyridine-3-sulfonamide The title compound was prepared by the method of Example 4(A) using N-(4-chloro-5-methyl-3-isoxazolyl)thieno[2,3-b]pyridine-3-sulfonamide (0.30 g, 0.91 mmoles), EtOAc (30 ml), DIEA (0.24 ml, 1.4 mmoles) and MEM-Cl (0.11 ml, 1.0 mmoles). Flash chromatography (40% EtOAc/hexanes) provided 0.23 g (59%) of the title compound as a light yellow oil.

C. N-(4-chloro-5-methyl-3-isoxazolyl)-N-(methoxyethoxymethyl)-2-[α-hydroxy-2-methyl-4,5-(methylenedioxy)-benzyl]thieno[2,3-b]pyridine-3-sulfonamide The title compound was prepared by the method of Example 4(B) using N-(4-chloro-5-methyl-3-isoxazolyl)-N-(methoxyethoxymethyl)thieno[2,3-b]pyridine-3-sulfonamide (0.23 g, 0.54 mmoles), THF (5 ml), t-BuLi (1.7 M, 0.41 ml, 0.70 mmoles) and 2-methyl-4,5-(methylenedioxy)benzaldehyde (0.13 g, 0.81 mmoles) [Example 6(A)]. Flash chromatography (40% EtOAc/hexanes) provided 0.11 g (36%) of the title compound as a light orange oil.

D. N-(4-chloro-5-methyl-3-isoxazolyl)-N-(methoxyethoxymethyl)-2-[2-methyl-4,5-(methylenedioxy)benzyl]thieno[2,3-b]pyridine-3-sulfonamide The title compound was prepared by the method of Example 5(A) using N-(4-chloro-5-methyl-3-isoxazolyl)-N-(methoxyethoxymethyl)-2-[α-hydroxy-2-methyl-4,5-(methylenedioxy)benzyl]thieno[2,3-b]pyridine-3-sulfonamide (0.11 g, 0.19 mmoles), $CH_2Cl_2$ (5 ml), triethyl silane (0.31 ml, 1.9 mmoles) and boron trifluoride etherate (0.12 ml, 0.97 mmoles). Flash chromatography (35% EtOAc/hexanes) provided 58 mg (53%) of the title compound as a tan solid.

E. N-(4-chloro-5-methyl-3-isoxazolyl)-2-[2-methyl-4,5-methyl-enedioxy)benzyl]thieno[2,3-b]pyridine-3-sulfonamide The title compound was prepared by the method of Example 4(D) using N-(4-chloro-5-methyl-3-isoxazolyl)-N-(methoxyethoxymethyl)-2-[2-methyl-4,5-(methylenedioxy)benzyl]thieno[2,3-b]pyridine-3-sulfonamide (58 mg, 0.10 mmoles), methanol (3 ml) and 4N HCl (1 ml). Recrystallization from chloroform and hexanes provided 40 mg (80%) of the title compound as a white solid, m.p. 189–191° C.

EXAMPLE 9

N-(4-chloro-3-methyl-5-isoxazolyl)-2-[2-(2-hydroxyethyl)-4,5-(methylenedioxy)benzyl]thieno[2,3-b]pyridine-3-sulfonamide A. N-(4-chloro-3-methyl-5-isoxazolyl)-N-(methoxyethoxymethyl)-2-[α-hydroxy-4,5-(methylenedioxy)-2-(2-{[(1,1-dimethylethyl)dimethylsilyl]oxy}ethyl)benzyl]thieno[2,3-b]pyridine-3-sulfonamide The title compound was prepared by the method of Example 4(B) using N-(4-chloro-3-methyl-5-isoxazolyl)-N-(methoxyethoxymethyl)thieno-[2,3-b]pyridine-3-sulfonamide (0.64 g, 1.5 mmoles) [Example 4(A)], THF (10 ml), t-BuLi (1.7 M, 1.2 ml, 2.0 mmoles), and 4,5-(methylenedioxy)-2-(2-{[(1,1-dimethylethyl)dimethylsilyl]oxy}ethyl)benzaldehyde (0.71 g, 2.3 mmoles; prepared according to Lin, et al. (1994) *J. Am. Chem. Soc.* 116:9791–9792). Flash chromatography (40% EtOAc/hexanes) provided 0.51 g (46%) of the title compound as a yellow solid.

B. N-(4-chloro-3-methyl-5-isoxazolyl)-N-(methoxyethoxymethyl)-2-[α-hydroxy-2-(2-hydroxyethyl)-4,5-(methylene-dioxy)benzyl]thieno [2,3-b]pyridine-3-sulfonamide A solution of N-(4-chloro-3-methyl-5-isoxazolyl)-N-(methoxyethoxy-methyl)-2 -[α-hydroxy-4,5-(methylenedioxy)-2-(2-{[(1,1-dimethylethyl)dimethylsilyl]oxy}ethyl)benzyl]thieno [2,3-b]pyridine-3-sulfonamide (0.29 g, 0.40 mmoles) in acetic acid (3 ml), $H_2O$ (1 ml) and THF (1 ml) was stirred at ambient temperature for 18 hours, then diluted with EtOAc (100 ml) and washed with sat. $NaHCO_3$ (2×200 ml). The organic layer was dried ($MgSO_4$), filtered and concentrated to collect 0.23 g (94%) of the title compound as a yellow oil.

C. N-(4-chloro-3-methyl-5-isoxazolyl)-N-(methoxyethoxymethyl)-2 -{α-acetoxy-2-[2-(acetoxy)ethyl]-4,5-(methylenedioxy)-benzyl}thieno[2,3-b]pyridine-3-sulfonamide To a solution of N-(4-chloro-3-methyl-5-isoxazolyl)-N-(methoxyethoxymethyl) -2-[α-hydroxy-2-(2-hydroxyethyl)-4,5-(methylene-dioxy)benzyl]thieno [2,3-b]pyridine-3-sulfonamide (0.11 g, 0.19 mmoles) in pyridine (2 ml) was added acetic anhydride (0.18 ml, 1.9 mmoles). The reaction solution was stirred 2 hours at ambient temperature, then diluted with EtOAc (50 ml) and washed with 2% HCl (2×100 ml). The organic layer was dried ($MgSO_4$), filtered and concentrated to collect 0.13 g (100%) of the title compound as a yellow oil.

D. N-(4-chloro-3-methyl-5-isoxazolyl)-N-(methoxyethoxymethyl)-2 -{2-[2-(acetoxy)ethyl]-4,5-(methylene-dioxy)benzyl}thieno[2,3-b]pyridine-3-sulfonamide The title compound was prepared by the method of Example 5(A) using N-(4-chloro-3-methyl-5-isoxazolyl)-N-(methoxyethoxymethyl)-2-{α-acetoxy-2 -[2-(acetoxy)ethyl]-4,5-(methylenedioxy)benzyl}thieno[2,3-b]-pyridine-3-sulfonamide (0.13 g, 0.19 mmoles), $CH_2Cl_2$ (3 ml), triethylsilane (0.30 ml, 1.9 mmoles) and boron trifluoride etherate (0.12 ml, 0.95 mmoles), giving 0.12 g (96%) of the title compound as a yellow oil.

E. N-(4-chloro-3-methyl-5-isoxazolyl)-2-[2-(2-hydroxyethyl)-4,5-(methylenedioxy)benzyl]thieno[2,3-b]pyridine-3-sulfonamide The title compound was prepared by the method of Example 4(D) using N-(4-chloro-3-methyl-5-isoxazolyl)-N-(methoxyethoxymethyl)-2-{2-[2 -(acetoxy)ethyl]-4,5-(methylenedioxy)benzyl}thieno[2,3-b]pyridine-3-sulfonamide (83 mg, 0.13 mmoles), methanol (3 ml) and 4N HCl (1 ml). Recrystallization from $CH_2Cl_2$/hexanes provided 55 mg (84%) of the title compound as a white solid, m.p. 104–106° C.

EXAMPLE 10

N-(4-chloro-3-methyl-5-isoxazolyl)-2-(1-naphthylmethyl)thieno[2,3-b]pyridine-3-sulfonamide A. N-(4-chloro-3-methyl-5-isoxazolyl)-N-(methoxyethoxymethyl)-2 -(α-hydroxynaphthlymethyl)thieno [2,3-b]pyridine-3-sulfonamide The title compound was prepared by the method of Example 4(B) using N-(4-chloro-3-methyl-5-isoxazolyl)-N-(methoxyethoxymethyl)thieno-[2,3 -b]pyridine-3-sulfonamide (0.15 g, 0.36 mmoles)[Example 4(A)], THF (3 ml), n-BuLi (2.5 M, 0.22 ml, 0.54 mmoles) and 1-naphthylaldehyde (0.10 ml, 0.72 mmoles). Flash chromatography (40% EtOAc/hexanes) provided 0.10 g (49%) of the title compound as a light yellow oil.

B. N-(4-chloro-3-methyl-5-isoxazolyl)-N-(methoxyethoxymethyl)-2 -(α-acetoxynaphthylmethyl)thieno[2,3-b]pyridine-3-sulfonamide The title compound was prepared by the method of Example 9(C) using N-(4-chloro-3-methyl-5-isoxazolyl)-N-(methoxyethoxymethyl)-2-(α-hydroxynaphthlymethyl)thieno [2,3-b]pyridine-3-sulfonamide (0.10 g, 0.18 mmoles), pyridine (3 ml) and acetic anhydride (0.5 ml). 97 mg (89%) of the title compound was isolated as a foamy yellow solid.

C. N-(4-chloro-3-methyl-5-isoxazolyl)-N-(methoxyethoxymethyl)-2-(naphthylmethyl)thieno [2,3-b]pyridine-3-sulfonamide The title compound was prepared by the method of Example 5(A) using N-(4-chloro-3-methyl-5-isoxazolyl)-N-(methoxyethoxymethyl)-2-(α-acetoxynaphthylmethyl)thieno [2,3-b]pyridine-3-sulfonamide (97 mg, 0.16 mmoles), $CH_2Cl_2$ (3 ml), triethylsilane (0.25 ml, 1.6 mmoles) and boron trifluoride etherate (0.19 ml, 1.6 mmoles). Flash chromatography (40% EtOAc/hexanes) provided 58 mg (66%) of the title compound as a yellow solid.

D. N-(4-chloro-3-methyl-5-isoxazolyl)-2-(naphthylmethyl)thieno-[2,3-b]pyridine-3-sulfonamide The title compound was prepared by the method of Example 4(D) using N-(4-chloro-3-methyl-5-isoxazolyl)-N-(methoxyethoxymethyl)-2-(naphthylmethyl)thieno [2,3-b]pyridine-3-sulfonamide (58 mg, 0.10 mmoles), methanol (2 ml) and 4N HCl (2 ml). Recrystallization from EtOAc/hexanes provided 30 mg (61%) of the title compound as a yellow crystalline solid, m.p. 165–168° C.

EXAMPLE 11

N-(4-chloro-3-methyl-5-isoxazolyl)-2-(2,6-dimethoxybenzyl)thieno[2,3-b]pyridine-3-sulfonamide A. N-(4-chloro-3-methyl-5-isoxazolyl)-N-(methoxyethoxymethyl)-2 -(α-hydroxy-2,6-dimethoxybenzyl)thieno[2,3-b]pyridine-3-sulfonamide The title compound was prepared by the method of Example 4(B) using N-(4-chloro-3-methyl-5-isoxazolyl)-N-(methoxyethoxymethyl)thieno [2,3-b]pyridine-3-sulfonamide (0.15 g, 0.35 mmoles) [Example 4(A)], THF (5 ml), n-BuLi (2.5 M, 0.16 ml, 0.41 mmoles) and 2,6-dimethoxybenzaldehyde (88 mg, 0.53 mmoles). Flash chromatography (50% EtOAc/hexanes) provided 0.13 g (62%) of the title compound as a pink oil.

B. N-(4-chloro-3-methyl-5-isoxazolyl)-N-(methoxyethoxymethyl)-2 -(2,6-dimethoxybenzyl)thieno[2,3-b]pyridine-3-sulfonamide The title compound was prepared by the method of Example 5(A) using N-(4-chloro-3-methyl-5-isoxazolyl)-N-(methoxyethoxymethyl)-2-(α-hydroxy-2,6-dimethoxybenzyl)thieno[2,3-b]pyridine-3-sulfonamide (0.13 g, 0.22 mmoles), $CH_2Cl_2$ (5 ml), triethylsilane (0.35 ml, 2.2 mmoles) and boron trifluoride etherate (0.16 ml, 1.3 mmoles). Flash chromatography (40% EtOAc/hexanes) provided 0.11 g (85%) of the title compound as a colorless oil.

C. N-(4-chloro-3-methyl-5-isoxazolyl)-2-(2,6-dimethoxybenzyl)-thieno [2,3-b]pyridine-3-sulfonamide The title compound was prepared by the method of Example 4(D) using N-(4-chloro-3-methyl-5-isoxazolyl)-N-(methoxyethoxymethyl)-2-(2,6-dimethoxybenzyl)thieno [2,3-b]pyridine-3-sulfonamide (0.11 g, 0.19 mmoles), methanol (5 ml) and 4N HCl (1 ml). Recrystallization from EtOAc/hexanes provided 35 mg (39%) of the title compound as a white precipitate, m.p. 66–71° C.

EXAMPLE 12

N-(4-chloro-3-methyl-5-isoxazolyl)-2-[3-(3,4-methylenedioxyphenyl)-propionyl]thieno [2,3-b] pyridine-3-sulfonamide A. 3-(3,4-methylenedioxyphenyl)propyl alcohol To a solution of 3-(3,4-methylenedioxyphenyl)propionic acid (1.0 g, 5.2 mmoles) in ether (100 ml) at 0° C. was added borane-tetrahydrofuran (1.0 M, 6.2 ml, 6.2 mmoles). The cooling bath was removed and 15 minutes later methanol (5 ml) was slowly added. One hour later the reaction was washed with $H_2O$ (200 ml), and then the organic layer was dried ($MgSO_4$), filtered and concentrated to collect 0.91 g (98%) of the title compound as a colorless oil.

B. 3-(3,4-methylenedioxyphenyl)propionaldehyde

To a mixture of 3-(3,4-methylenedioxyphenyl)propyl alcohol (0.26 g, 1.4 mmoles) and celite in $CH_2Cl_2$ (7 ml) was added PCC (0.46 g, 2.2 mmoles). The brown reaction mixture was filtered through a plug of celite 1.5 hours later and then concentrated. The brown residue was subjected to flash chromatography (20% EtOAc/hexanes) to provide 0.20 g (77%) of the title compound as a light yellow oil.

C. N-(4-chloro-3-methyl-5-isoxazolyl)-N-(methoxyethoxymethyl)-2-[1-hydroxy-3-(3,4-methylenedioxyphenyl)propyl]thieno[2,3-10b]pyridine-3-sulfonamide The title compound was prepared by the method of Example 4(B) using N-(4-chloro-3-methyl-5-isoxazolyl)-N-(methoxyethoxymethyl)thieno [2,3-b]pyridine (0.40 g, 0.96 mmoles)[Example 4(A)], THF (10 ml), n-BuLi (2.5 M, 0.42 ml, 1.1 mmoles) and 3-(3,4-15 methylenedioxyphenyl) propionaldehyde (0.20 g, 1.1 mmoles). Flash chromatography (50% EtOAc/hexanes) provided 0.51 g (89%) of the title compound as a light yellow solid.

D. N-(4-chloro-3-methyl-5-isoxazolyl)-N-(methoxyethoxymethyl)-2-[3-(3,4-methylenedioxyphenyl)propionyl]thieno[2,3-b]pyridine-3-sulfonamide The title compound was prepared by the method of Example 12(B) using N-(4-chloro-3-methyl-5-isoxazolyl)-N-(methoxyethoxymethyl)-2-[1-hydroxy-3-(3,4-methylenedioxyphenyl)propyl]thieno[2,3-b]pyridine-3-sulfonamide (0.51 g, 0.85 mmoles), $CH_2Cl_2$ (20 ml), celite, and PCC (0.27 g, 1.3 mmoles) except the reaction mixture was stirred 24 hours prior to filtering. Flash chromatography (40% EtOAc/hexanes) provided 0.37 g (74%) of the title compound as a yellow oil/solid.

E. N-(4-chloro-3-methyl-5-isoxazolyl)-2-[3-(3,4-methylenedioxy-phenyl)propionyl]thieno[2,3-b]pyridine-3-sulfonamide The title compound was prepared by the method of Example 4(D) using N-(4-chloro-3-methyl-5-isoxazolyl)-N-(methoxyethoxymethyl)-2-[3-(3,4-methylenedioxyphenyl) propionyl]thieno[2,3-b]pyridine-3-sulfonamide (0.26 9, 0.44 mmoles), methanol (7 ml) and 4N HCl (1.5 ml), giving 0.21 g (97%) of the title compound as a yellow foamy solid, m.p. 40–45° C.

EXAMPLE 13

Assays for Identifying Compounds that Exhibit Endothelin Antagonistic and/or Agonist Activity Compounds that are potential endothelin antagonists are identified by testing their ability to compete with $^{125}$I-labeled ET-1 for binding to human $ET_A$ receptors or $ET_B$ receptors present on isolated cell membranes. The effectiveness of the test compound as an antagonist or agonist of the biological tissue response of endothelin can also be assessed by measuring the effect on endothelin induced contraction of isolated rat thoracic aortic rings. The ability of the compounds to act as antagonists or agonists for $ET_B$ receptors can be assess by testing the ability of the compounds are to inhibit endothelin-1 induced prostacyclin release from cultured bovine aortic endothelial cells.

A. Endothelin Binding Inhibition—Binding Test #1: Inhibition of binding to $ET_A$ Receptors TE 671 cells (ATCC Accession No. HTB 139) express $ET_A$ receptors. These cells were grown to confluence in T-175 flasks. Cells from multiple flasks were collected by scraping, pooled and centrifuged for 10 min at 190×g. The cells were resuspended in phosphate buffered saline (PBS) containing 10 mM EDTA using a Tenbroeck homogenizer. The suspension was centrifuged at 4° C. at 57,800×g for 15 min, the pellet was resuspended in 5 ml of buffer A (5 mM HEPES buffer, pH 7.4 containing aprotinin (100 KIU/ml)) and then frozen and thawed once. 5 ml of Buffer B (5 mM HEPES Buffer, pH 7.4 containing 10 mM $MnCl_2$ and 0.001% deoxyribonuclease Type 1) was added, the suspension mixed by inversion and then incubated at 37° C. for 30 minutes. The mixture was centrifuged at 57,800×g as described above, the pellet washed twice with buffer A and then resuspended in buffer C (30 mM HEPES buffer, pH 7.4 containing aprotinin (100 KIU/ml) to give a final protein concentration of 2 mg/ml and stored at −70° C. until use.

The membrane suspension was diluted with binding buffer (30 mM HEPES buffer, pH 7.4 containing 150 mM NaCl, 5 mM $MgCl_2$, 0.5% Bacitracin) to a concentration of 8 µg/50 µl. $^{125}$I-endothelin-1 (3,000 cpm, 50 ml) was added to 50 µl of either: (A) endothelin-1 (for non specific binding) to give a final concentration 80 nM); (B) binding buffer (for total binding); or (C) a test compound (final concentration 1 nM to 100 µM). The membrane suspension (50 µl), containing up to 8 µg of membrane protein, was added to each of (A), (B), or (C). Mixtures were shaken, and incubated at 4° C. for 16–18 hours, and then centrifuged at 4° C. for 25 min at 2,500×g. Alternatively, the incubation was conducted at 24° C. When incubated at 24° C., the $IC_{50}$ concentrations are 2- to 10-fold higher than when the incubation is conducted at 4° C. This, must be kept in mind when comparing $IC_{50}$ concentrations among compounds provided herein.

The supernatant, containing unbound radioactivity, was decanted and the pellet counted on a Genesys multiwell gamma counter. The degree of inhibition of binding (D) was calculated according to the following equation:

$$\%D = 100 - \frac{(C) - (A)}{(B) - (A)} \times 100$$

Each test was generally performed in triplicate.

B. Endothelin Binding Inhibition—Binding Test #2: Inhibition of Binding to $ET_B$ Receptors COS7 cells were transfected with DNA encoding the $ET_B$ receptor, The resulting cells, which express the human $ET_B$ receptor, were grown to confluence in T-150 flasks. Membrane was prepared as described above. The binding assay was performed as described above using the membrane preparation diluted with binding buffer to a concentration of 1 µg/50 µl.

Briefly, the COS7 cells, described above, that had been transfected with DNA encoding the $ET_B$ receptor and express the human $ET_B$ receptor on their surfaces were grown to confluence in T-175 flasks. Cells from multiple flasks were collected by scraping, pooled and centrifuged for 10 min at 190×g. The cells were resuspended in phosphate buffered saline (PBS) containing 10 mM EDTA using a Tenbroeck homogenizer. The suspension was centrifuged at 4° C. 57,800×g for 15 min, the pellet was resuspended in 5 ml of buffer A (5mM HEPES buffer, pH 7.4 containing aprotinin (100 KIU/ml)) and then frozen and thawed once. Five ml of Buffer B (5 mM HEPES Buffer, pH 7.4 containing 10 mM $MnCl_2$ and 0.001% deoxyribonuclease Type 1) was added, the suspension mixed by inversion and then incubated at 37° C. for 30 minutes. The mixture was centrifuged at 57,800×g as described above, the pellet washed twice with buffer A and then resuspended in buffer C (30 mM HEPES buffer, pH 7.4 containing aprotinin (100 KIU/ml) to give a final protein concentration of 2 mg/ml.

The binding assay was performed as described above using the membrane preparation diluted to give 1 $\mu$g/50, $\mu$l of binding buffer.

C. Test for Activity Against Endothelin-induced Contraction of Isolated Rat Thoracic Aortic Rings The effectiveness of the test compound as an antagonist or agonist of the biological tissue response of endothelin also is assessed by measuring the effect on endothelin induced contraction of isolated rat thoracic aortic rings (see, e.g., Borges et al. (1989) *Eur. J. Pharmacol.* 165:223–230) or by measuring the ability to contract the tissue when added alone.

Compounds to be tested are prepared as 100 $\mu$M stocks. If necessary to effect dissolution, the compounds are first dissolved in a minimum amount of DMSO and diluted with 150 mM NaCl. Because DMSO can cause relaxation of the aortic ring, control solutions containing varying concentrations of DMSO were tested.

The thoracic portion of the adult rat aorta is excised, the endothelium abraded by gentle rubbing and then cut into 3 mm ring segments. Segments are suspended under a 2 g preload in a 10 ml organ bath filled with Krebs'—Henseleit solution saturated with a gas mixture of 95% $O_2$ and 5% $CO_2$ (118 mM NaCl, 4.7 mM KCl, 1.2 mM $MgSO_4$, 1.2 mM $KH_2PO_4$, 25 mM $NaHCO_3$, 2.5 mM $CaCl_2$, 10 mM D-glucose).

There is a correlation between activity as an antagonist of endothelin-induced thoracic aortic ring contraction and activity as an inhibitor of binding of endothelin to endothelin receptors. The $pA_2$ is a linear function of the log of the $IC_{50}$.

D. Assay for Identifying Compounds that Have Agonist and/or Antagonistic Activity Against $ET_B$ Receptors 1. Stimulation of Prostacyclin Release Since endothelin-1 stimulates the release of prostacyclin from cultured bovine aortic endothelial cells, the compounds that have agonist or antagonist activity are identified by their ability to inhibit endothelin-1 induced prostacyclin release from such endothelial cells by measuring 6-keto $PGF_{1\alpha}$ substantially as described by (Filep et al. (1991) *Biochem. Biophys. Res. Commun.* 177:171–176. Bovine aortic cells are obtained from collagenase-treated bovine aorta, seeded into culture plates, grown in Medium 199 supplemented with heat inactivated 15% fetal calf serum, and L-glutamine (2 mM), penicillin, streptomycin and fungizone, and subcultured at least four times. The cells are then seeded in six-well plates in the same medium. Eight hours before the assay, after the cells reach confluence, the medium is replaced. The cells are then incubated with a) medium alone, b) medium containing endothelin-1 (10 nM), c) test compound alone, and d) test compound+endothelin-1 (10 nM).

After a 15 min incubation, the medium is removed from each well and the concentrations of 6-keto $PGF_{1\alpha}$ are measured by a direct immunoassay. Prostacyclin production is calculated as the difference between the amount of 6-keto $PGF_{1\alpha}$ released by the cells challenged with the endothelin-1 minus the amount released by identically treated unchallenged cells. Compounds that stimulate 6-keto $PGF_{1\alpha}$ release possess agonist activity and those which inhibit endothelin-16-keto $PGF_{1\alpha}$, release possess antagonist activity.

2. Inhibition of Sarafotoxin 6c Induced Contraction

Sarafotoxin 6c is a specific $ET_B$ antagonist that contracts rat fundal stomach strips. The effectiveness of test compounds to inhibit this sarafotoxin 6c-induced contraction of rat fundal stomach strips is used as a measure $ET_B$ antagonist activity. Two isolated rat fundal stomach strips are suspended under a 1 g load in a 10 ml organ bath filled with Krebs' Henseleit solution containing 10 $\mu$M cyclo(D-Asp-Pro-D-Val-Leu-D-Trp) (BQ-123; see, U.S. Pat. No. 5,114, 918 to Ishikawa et al.), 5 $\mu$M indomethacin, and saturated with a gas mixture of 95% $O_2$/5% $CO_2$. Changes in tension are measured isometrically and recorded using a Grass Polygraph coupled to a force transducer. Sarafotoxin 6c is added cumulatively to one strip while the second strip is preincubated for 15 min with a test compound prior to addition of cumulative doses of sarafotoxin 6c. The effects of the test compounds on the concentration-response curve for sarafotoxin 6c are examined.

E. Deoxycorticosterone Acetate (DOCA)-salt Hypertensive Rat Model for Assessing in vivo Activity of Selected Compounds Selected compounds disclosed herein are tested for activity in the deoxycorticosterone acetate (DOCA)-salt hypertensive rat model. To perform these tests, silastic MDX4-4210 elastomer implants containing 47 mg (DOCA) are prepared according to the method of Ornmsbee et al. ((1973) the *J. Pharm. Sci.* 62:255–257). Briefly, DOCA is incorporated into silicon rubber implants for sustained release. To prepare the implants the DOCA is incorporated into unpolymerized silicone rubber, catalyst is added and the mixture is cast in a hemicylindrical shape.

Sprague Dawley rats (7–8 weeks old) are unilaterally nephrectomized under ketamine anesthesia and a DOCA-implant is placed on the left lateral dorsal abdomen of the animal. The rats are allowed to recover for about three weeks. During recovery they are permitted free access to normal rat chow and 0.9% NaCl drinking solution in place of drinking water. The rats develop hypertension within 3 weeks.

All animals are used in the tests between 21 and 30 days post surgery. The mean arterial blood pressure in these animals ranges from about 165–200 mm Hg.

On the day of experimentation, catheters are inserted under brevital anesthesia into the right femoral artery for measurement of blood pressure, and into the right femoral vein for administration of a selected compound. The animals are placed in a restrainer and allowed to recover for a minimum of 60 mm or until a steady mean arterial blood pressure is recorded. At that time, the selected compound or control vehicle is administered either intravenously, as a 60 minute infusion, or orally by oral gavage. Blood pressure was recorded continuously for a further 10 hrs.

F. Effect of Intravenous Administration on ET-1-induced Pressor Responses in Conscious, Autonomically Blocked Rats; a Model for Assessing in vivo Activity of Selected Compounds Male Sprague Dawley rats (250–450 g) are anesthetized (Brevital 50 mg/kg, IP) and cannulae were placed in the femoral artery to measure mean arterial pressure (MAP) and in the femoral vein for intravenous drug administration. Animals are placed in a restrainer and allowed to regain consciousness. Thirty minutes later autonomic blockade is administered (atropine methyl nitrate, 3 mg/kg, IV, followed by propranalol, 2 mg/kg, IV). An hour later animals receive a bolus injection of vehicle (0.5 ml) followed thirty minutes later by intravenous bolus administration of ET-1 (Control, 1 μg/kg). Following recovery from this challenge, test compounds are administered by intravenous bolus administration (0.5 ml) and then re-challenged with ET-1 thirty minutes later. Results are expressed as the percent inhibition of the ET-1-induced pressor response after administration of the test compound compared to the pressor response induced by the control ET-1 challenge. In some cases a third ET-1 challenge is administered ninety minutes after administration of the test compound.

G. Results

The $IC_{50}$ for each of the compounds of the preceding Examples for $ET_A$ and $ET_B$ receptors has been measured. Almost all of the compounds have an $IC_{50}$ of less than 10/μM and many have an $IC_{50}$ less than about 1 μM for either or both of the $ET_A$ and $ET_B$ receptors. A number of the compounds have an $IC_{50}$ for one receptor sub-type that is substantially less (at least 10-fold or more) than for the other receptor sub-type. Thus, these compounds are selective for either the $ET_A$ receptor sub-type or the $ET_B$ receptor sub-type.

Since modifications will be apparent to those of skill in this art, it is intended that this invention be limited only by the scope of the appended claims.

We claim:

1. A method for the treatment of glaucoma, comprising administering an effective amount of one or more compounds of formula (I):

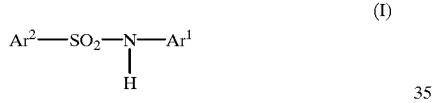

(I)

or pharmaceutically acceptable salts thereof, wherein:

$Ar^1$, which contains from 1 to 30 carbon atoms, is selected from the group consisting of alkyl, alkenyl, alkynyl, aryl, heterocyclyl and fused bicyclic or tricyclic rings, wherein the alkyl, alkenyl and alkynyl groups may be straight or branched chains, or straight or branched chains that include cyclic portions; and $Ar^2$ is a group of formula:

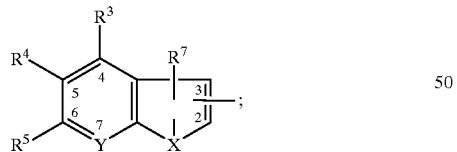

Y is N or $O^+$; X is S, O, or $NR^{11}$ in which $R^{11}$, which is hydrogen or contains up to about 30 carbon atoms, is selected from the group consisting of hydrogen, alkyl, alkenyl, alkynyl, aryl, alkylaryl, heterocyclyl, aralkyl, aralkoxy, cycloalkyl, cycloalkenyl, cycloalkynyl, C(O)$R^{15}$ and S(O)$_n R^{15}$ in which n is 0–2; and $R^{15}$, which is selected independently from $R^{11}$, is selected from the group consisting of hydrogen, alkyl, alkenyl, alkynyl, aryl, alkylaryl, heterocyclyl, aralkyl, aralkoxy, cycloalkyl, cycloalkenyl and cycloalkynyl;

$R^3$, $R^4$ and $R^5$ are selected from (i), (ii), (iii) or (iv):

(i) $R^3$, $R^4$ and $R^5$ are each selected independently from among H, NHOH, $NH_2$, $NO_2$, $N_3$, halide, pseudohalide, alkyl, alkenyl, alkynyl, alkylaryl, aryloxy, aryl, heteroaryl, alkoxy, alkylamino, alkylthio, alkoxyalkyl, alkylsulfinyl, alkylsulfonyl, aryloxy, arylamino, arylthio, arylsulfinyl, arylsulfonyl, haloalkyl, haloaryl, alkoxycarbonyl, alkylcarbonyl, arylcarbonyl, formyl and amido, where the alkyl, alkenyl and alkynyl portions are straight or branched chains of from about 1 up to about 10 carbons, and the aryl portions contain from 3 up to about 10 carbons; or (ii) two of $R^3$, $R^4$ and $R^5$ form 1,3-butadienyl, 4-dimethylamino -1,3-butadienyl, 1-chloro-1,3-butadienyl, 1-aza-1,3-butadienyl or 2-aza-1,3-butadienyl groups or form alkylenedioxy; and the other of $R^3$, $R^4$ and $R^5$ is as defined in (i); or (iii) two of $R^3$, $R^4$ and $R^5$ are independently selected from alkyl, alkoxy, halide, aminoalkyl and dialkylaminoalkyl, in which the alkyl and alkoxy groups contain from 1 to 10 carbons, and are straight or branched chains and the other is H; or (iv) any two of $R^3$, $R^4$ and $R^5$, which are each selected as in (i), form fused carbocyclic or heterocyclic rings and the other is selected as in (i); and $R^7$ is hydrogen or contains up to about 50 carbon atoms and is selected from hydrogen, halide, pseudohalide, alkyl, alkoxy, alkenyl, alkynyl, aryl, aryloxy, heterocyclyl, aralkyl, aralkoxy, cycloalkyl, cycloalkenyl, cycloalkynyl, OH, CN, C(O)$R^{18}$, CO$_2R^{18}$, (CH$_2$)$_r$COR$^{18}$, (CH$_2$)$_r$CO(CH$_2$)$_s R^{18}$, SH, (CH$_2$)$_r R^{18}$, S(O)$_n R^{18}$ in which n is 0–2, and r is 0 to 6, HNOH, $NR^{18}R^{19}$, $NO_2$, $N_3$, $OR^{18}$, $R^{19}NCOR^{18}$ and $CONR^{19}R^{18}$, in which $R^{19}$ is selected from hydrogen, alkyl, alkenyl, alkynyl, aryl, alkylaryl, alkoxy, aryloxy, heterocyclyl, aralkyl, aralkoxy, cycloalkyl, cycloalkenyl, cycloalkynyl, C(O)$R^{20}$ and S(O)$_n R^{20}$ in which n is 0–2; and $R^{18}$ and $R^{20}$ are independently selected from hydrogen, alkyl, alkenyl, alkynyl, aryl, alkylaryl, heterocyclyl, alkoxy, aryloxy, aralkyl, aralkoxy, cycloalkyl, cycloalkenyl and cycloalkynyl; and any of the groups set forth for $R^7$ is unsubstituted or substituted with any substituents set forth for Z, which is hydrogen, halide, pseudohalide, alkyl, alkoxy, alkenyl, alkynyl, aryl, aryloxy, heterocyclyl, aralkyl, aralkoxy, cycloalkyl, cycloalkenyl, cycloalkynyl, OH, CN, C(O)$R^{21}$, CO$_2R^{21}$, SH, S(O)$_n R^{21}$ in which n is 0–2, NHOH, $NR^{22}R^{21}$, $NO_2$, $N_3$, $OR^{21}$, $R^{22}NCOR^{21}$ or $CONR^{22}R^{21}$; $R^{22}$ is selected from hydrogen, alkyl, alkenyl, alkynyl, aryl, alkylaryl, heterocyclyl, aralkyl, alkoxy, aralkoxy, cycloalkyl, cycloalkenyl, cycloalkynyl, C(O)$R^{23}$ and S(O)$_n R^{23}$ in which n is 0–2; and $R^{21}$ and $R^{23}$ are independently selected from hydrogen, alkyl, alkenyl, alkynyl, aryl, alkylaryl, heterocyclyl, aralkyl, aralkoxy, cycloalkyl, cycloalkenyl and cycloalkynyl, wherein the effective amount is sufficient to ameliorate one or more of the symptoms of the disease.

2. The method of claim 1, wherein the compound of formula (I) has the formula:

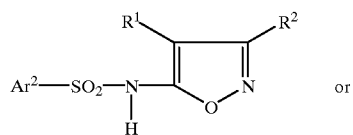

or

-continued

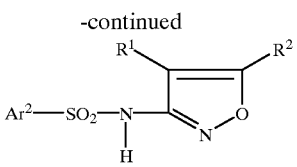

wherein
R¹ and R² are either (i), (ii) or (iii) as follows:
(i) R¹ and R² are each independently selected from H, NH₂, NO₂, halide, pseudohalide, alkyl, alkenyl, alkynyl, aryl, arylalkyl, heteroaryl, alkoxy, alkylamino, alkylthio, haloalkyl, alkylsulfinyl, alkylsulfonyl, aryloxy, arylamino, arylthio, arylsulfinyl, arylsulfonyl, haloalkyl, haloaryl, alkoxycarbonyl, alkylcarbonyl, aminocarbonyl, arylcarbonyl, formyl, substituted or unsubstituted amido and substituted or unsubstituted ureido, in which the alkyl, alkenyl and alkynyl portions contain from 1 up to about 14 carbon atoms and are either straight or branched chains or cyclic, and the aryl portions contain from about 4 to about 16 carbons, except that R² is not halide or pseudohalide; or, (ii) R¹ and R² together form —(CH₂)$_n$, where n is 3 to 6; or,
(iii) R¹ and R² together form 1,3-butadienyl; and
Ar² has the structure:

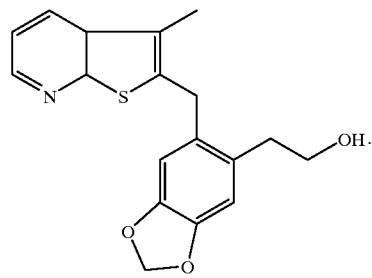

3. The method of claim 2, wherein R¹ is lower alkyl or halide; and R² is loweralkyl, halo loweralkyl, or hydrogen.

* * * * *

UNITED STATES PATENT AND TRADEMARK OFFICE
CERTIFICATE OF CORRECTION

PATENT NO. : 6,545,014 B2
DATED : April 8, 2003
INVENTOR(S) : Verner, E. J.

It is certified that error appears in the above-identified patent and that said Letters Patent is hereby corrected as shown below:

Title page,
Item [62], Related U.S. Application Data, please replace "1991" with -- 1999 --;
Item [56], References Cited, please add the following to the
OTHER PUBLICATIONS:
 -- Texas Biotechnology Reports Additional Positive Phase IIA Trial Results in Congestive Heart Failure, Houston, TX, July 21, 1998For Immediate Release, (available at http://www.tbc.com/press/pr072298.html on 1/13/99) --;
Item [57], ABSTRACT,
Please replace "pyrmidinyl" with -- pyrimidinyl --;

Column 1,
Line 6, please replace ""THIENO-PHRIDINE" with -- "THIENO-PYRIDINE --;

Column 39, line 28 through Column 40, line 57,

Please delete claim 1 and replace with the following claim:
 — 1. A method for the treatment of glaucoma, comprising administering an effective amount of one or more compounds of formula (I):

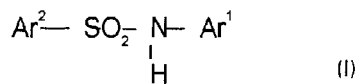

UNITED STATES PATENT AND TRADEMARK OFFICE
CERTIFICATE OF CORRECTION

PATENT NO. : 6,545,014 B2
DATED : April 8, 2003
INVENTOR(S) : Verner, E. J.

It is certified that error appears in the above-identified patent and that said Letters Patent is hereby corrected as shown below:

or pharmaceutically acceptable salts thereof, wherein:

$Ar^1$, which contains from 1 to 30 carbon atoms, is selected from the group consisting of alkyl, alkenyl, alkynyl, aryl, heterocyclyl and fused bicyclic or tricyclic rings, wherein the alkyl, alkenyl and alkynyl groups may be straight or branched chains, or straight or branched chains that include cyclic portions; and $Ar^2$ is a group of formula:

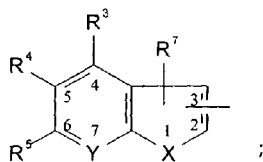

Y is N or $O^+$; X is S, O, or $NR^{11}$ in which $R^{11}$, which is hydrogen or contains up to about 30 carbon atoms, is selected from the group consisting of hydrogen, alkyl, alkenyl, alkynyl, aryl, alkylaryl, heterocyclyl, aralkyl, aralkoxy, cycloalkyl, cycloalkenyl, cycloalkynyl, $C(O)R^{15}$ and $S(O)_nR^{15}$ in which n is 0-2; and $R^{15}$, which is selected independently from $R^{11}$, is selected from the group consisting of hydrogen, alkyl, alkenyl, alkynyl, aryl, alkylaryl, heterocyclyl, aralkyl, aralkoxy, cycloalkyl, cycloalkenyl and cycloalkynyl;

$R^3$, $R^4$ and $R^5$ are selected from (i), (ii), (iii) or (iv):

(i) $R^3$, $R^4$ and $R^5$ are each selected independently from among H, NHOH, $NH_2$, $NO_2$, $N_3$, halide, pseudohalide, alkyl, alkenyl, alkynyl, alkylaryl, aryloxy, aryl, heteroaryl, alkoxy, alkylamino, alkylthio, alkoxyalkyl, alkylsulfinyl, alkylsulfonyl, aryloxy, arylamino, arylthio, arylsulfinyl, arylsulfonyl, haloalkyl, haloaryl, alkoxycarbonyl, alkylcarbonyl, arylcarbonyl, formyl and amido, where the alkyl, alkenyl and alkynyl portions are straight or branched chains of from about 1 up to about 10 carbons, and the aryl portions contain from 3 up to about 10 carbons; or (ii) two of $R^3$, $R^4$ and $R^5$ form 1,3-butadienyl, 4-dimethylamino-1,3-butadienyl, 1-chloro-1,3-butadienyl, 1-aza-1,3-butadienyl or 2-aza-1,3-butadienyl groups or form alkylenedioxy; and the other of $R^3$, $R^4$ and $R^5$ is as defined in (i); or (iii) two of $R^3$, $R^4$ and $R^5$ are independently selected from alkyl, alkoxy, halide, aminoalkyl and dialkylaminoalkyl, in which the alkyl and alkoxy groups contain from 1 to 10 carbons, and are straight or branched chains and the other is H; or (iv) any two of $R^3$, $R^4$ and $R^5$, which are each selected as in (i), form fused carbocyclic or heterocyclic rings and the other is selected as in (i); and $R^7$ is hydrogen or contains up to about 50 carbon atoms and is selected from hydrogen, halide, pseudohalide, alkyl, alkoxy, alkenyl, alkynyl, aryl, aryloxy, heterocyclyl, aralkyl,

UNITED STATES PATENT AND TRADEMARK OFFICE
CERTIFICATE OF CORRECTION

PATENT NO. : 6,545,014 B2
DATED : April 8, 2003
INVENTOR(S) : Verner, E. J.

It is certified that error appears in the above-identified patent and that said Letters Patent is hereby corrected as shown below:

aralkoxy, cycloalkyl, cycloalkenyl, cycloalkynyl, OH, CN, $C(O)R^{18}$, $CO_2R^{18}$, $(CH_2)_rCOR^{18}$, $(CH_2)_rCO(CH_2)_sR^{18}$, SH, $(CH_2)_rR^{18}$, $S(O)_nR^{18}$ in which n is 0-2, and r and s are each independently 0 to 6, HNOH, $NR^{18}R^{19}$, $NO_2$, $N_3$, $OR^{18}$, $R^{19}NCOR^{18}$ and $CONR^{19}R^{18}$, in which $R^{19}$ is selected from hydrogen, alkyl, alkenyl, alkynyl, aryl, alkylaryl, alkoxy, aryloxy, heterocyclyl, aralkyl, aralkoxy, cycloalkyl, cycloalkenyl, cycloalkynyl, $C(O)R^{20}$ and $S(O)_nR^{20}$ in which n is 0-2; and $R^{18}$ and $R^{20}$ are independently selected from hydrogen, alkyl, alkenyl, alkynyl, aryl, alkylaryl, heterocyclyl, alkoxy, aryloxy, aralkyl, aralkoxy, cycloalkyl, cycloalkenyl and cycloalkynyl; and any of the groups set forth for $R^7$ is unsubstituted or substituted with any substituents set forth for Z, which is hydrogen, halide, pseudohalide, alkyl, alkoxy, alkenyl, alkynyl, aryl, aryloxy, heterocyclyl, aralkyl, aralkoxy, cycloalkyl, cycloalkenyl, cycloalkynyl, OH, CN, $C(O)R^{21}$, $CO_2R^{21}$, SH, $S(O)_nR^{21}$ in which n is 0-2, NHOH, $NR^{22}R^{21}$, $NO_2$, $N_3$, $OR^{21}$, $R^{22}NCOR^{21}$ or $CONR^{22}R^{21}$; $R^{22}$ is selected from hydrogen, alkyl, alkenyl, alkynyl, aryl, alkylaryl, heterocyclyl, aralkyl, alkoxy, aralkoxy, cycloalkyl, cycloalkenyl, cycloalkynyl, $C(O)R^{23}$ and $S(O)_nR^{23}$ in which n is 0-2; and $R^{21}$ and $R^{23}$ are independently selected from hydrogen, alkyl, alkenyl, alkynyl, aryl, alkylaryl, heterocyclyl, aralkyl, aralkoxy, cycloalkyl, cycloalkenyl and cycloalkynyl,
wherein the effective amount is sufficient to ameliorate one or more of the symptoms of the disease.— —

Signed and Sealed this

Twenty-third Day of September, 2003

JAMES E. ROGAN
*Director of the United States Patent and Trademark Office*